(12) United States Patent
Horstmeyer et al.

(10) Patent No.: US 9,983,397 B2
(45) Date of Patent: May 29, 2018

(54) APERTURE SCANNING FOURIER PTYCHOGRAPHIC IMAGING

(71) Applicant: California Institute of Technology, Pasadena, CA (US)

(72) Inventors: Roarke W. Horstmeyer, Palo Alto, CA (US); Guoan Zheng, Vernon, CT (US); Xiaoze Ou, Pasadena, CA (US); Changhuei Yang, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days. days.

(21) Appl. No.: 15/206,859

(22) Filed: Jul. 11, 2016

(65) Prior Publication Data

US 2016/0320595 A1     Nov. 3, 2016

Related U.S. Application Data

(63) Continuation of application No. 14/448,850, filed on Jul. 31, 2014, now Pat. No. 9,426,455.

(Continued)

(51) Int. Cl.
*G02B 21/00* (2006.01)
*H04N 13/04* (2006.01)
(Continued)

(52) U.S. Cl.
CPC ......... *G02B 21/008* (2013.01); *G01N 23/205* (2013.01); *G01T 1/185* (2013.01);
(Continued)

(58) Field of Classification Search
CPC .............. G02B 21/008; G02B 21/0032; G02B 21/006; G02B 21/0056; G02B 21/0048
See application file for complete search history.

(56) References Cited

U.S. PATENT DOCUMENTS 5,475,527 A    12/1995  Hackel et al.
6,144,365 A    11/2000  Young et al.
(Continued)

FOREIGN PATENT DOCUMENTS

CN    101408623 A    4/2009
CN    101868740 A    10/2010
(Continued)

OTHER PUBLICATIONS

U.S. Appl. No. 15/081,659, filed Mar. 25, 2016 entitled "Fourier Ptychographic Retinal Imaging Methods and Systems".
U.S. Appl. No. 15/160,941, filed May 20, 2016 entitled "Laser-Based Fourier Ptychographic Imaging Systems and Methods".
U.S. Office Action dated Oct. 5, 2015 in U.S. Appl. No. 14/065,305.
U.S. Notice of Allowance dated Dec. 4, 2015 in U.S. Appl. No. 14/065,305.

(Continued)

*Primary Examiner* — Jonathan Hansen
(74) *Attorney, Agent, or Firm* — Sheila Martinez-Lemke; Weaver Austin Villeneuve & Sampson LLP

(57) ABSTRACT

Certain aspects pertain to aperture-scanning Fourier ptychographic imaging devices comprising an aperture scanner that can generate an aperture at different locations at an intermediate plane of an optical arrangement, and a detector that can acquire lower resolution intensity images for different aperture locations, and wherein a higher resolution complex image may be constructed by iteratively updating regions in Fourier space with the acquired lower resolution images.

22 Claims, 12 Drawing Sheets

Related U.S. Application Data

(60) Provisional application No. 61/860,786, filed on Jul. 31, 2013, provisional application No. 61/868,967, filed on Aug. 22, 2013.

(51) Int. Cl.
    *G01N 23/205*   (2018.01)
    *G01T 1/185*    (2006.01)
    *G01T 3/00*     (2006.01)
    *G02B 21/16*    (2006.01)
    *G02B 21/36*    (2006.01)

(52) U.S. Cl.
    CPC ............ *G01T 3/008* (2013.01); *G02B 21/006* (2013.01); *G02B 21/0032* (2013.01); *G02B 21/0048* (2013.01); *G02B 21/0056* (2013.01); *G02B 21/16* (2013.01); *G02B 21/367* (2013.01); *H04N 13/0459* (2013.01)

(56) References Cited

U.S. PATENT DOCUMENTS

| | | | |
|---|---|---|---|
| 6,154,196 A | 11/2000 | Fleck et al. | |
| 6,320,648 B1 | 11/2001 | Brueck et al. | |
| 6,747,781 B2 | 6/2004 | Trisnadi | |
| 6,905,838 B1 | 6/2005 | Bittner | |
| 7,436,503 B1 | 10/2008 | Chen et al. | |
| 7,460,248 B2 | 12/2008 | Kurtz et al. | |
| 7,706,419 B2 | 4/2010 | Wang et al. | |
| 7,787,588 B1 | 8/2010 | Yun et al. | |
| 8,271,521 B2 | 9/2012 | Vadon et al. | |
| 8,313,031 B2 | 11/2012 | Vinogradov | |
| 8,497,934 B2 * | 7/2013 | Milnes ................... | G02B 27/22 348/363 |
| 8,624,968 B1 | 1/2014 | Hersee et al. | |
| 8,942,449 B2 | 1/2015 | Maiden | |
| 9,029,745 B2 | 5/2015 | Maiden | |
| 9,426,455 B2 | 8/2016 | Horstmeyer et al. | |
| 9,497,379 B2 | 11/2016 | Ou et al. | |
| 9,829,695 B2 | 11/2017 | Kim et al. | |
| 9,864,184 B2 | 1/2018 | Ou et al. | |
| 9,892,812 B2 | 2/2018 | Zheng et al. | |
| 2001/0055062 A1 | 12/2001 | Shioda et al. | |
| 2002/0141051 A1 | 10/2002 | Vogt et al. | |
| 2003/0116436 A1 | 6/2003 | Amirkhanian et al. | |
| 2004/0146196 A1 | 7/2004 | Van Heel | |
| 2004/0190762 A1 | 9/2004 | Dowski, Jr. et al. | |
| 2005/0211912 A1 | 9/2005 | Fox | |
| 2006/0098293 A1 | 5/2006 | Garoutte et al. | |
| 2006/0173313 A1 | 8/2006 | Liu et al. | |
| 2006/0291707 A1 | 12/2006 | Kothapalli et al. | |
| 2007/0057184 A1 | 3/2007 | Uto et al. | |
| 2007/0133113 A1 | 6/2007 | Minabe et al. | |
| 2007/0159639 A1 | 7/2007 | Teramura et al. | |
| 2007/0171430 A1 | 7/2007 | Tearney et al. | |
| 2007/0189436 A1 | 8/2007 | Goto et al. | |
| 2008/0101664 A1 | 5/2008 | Perez | |
| 2009/0046164 A1 | 2/2009 | Shroff et al. | |
| 2009/0079987 A1 | 3/2009 | Ben-Ezra et al. | |
| 2009/0125242 A1 | 5/2009 | Choi et al. | |
| 2009/0284831 A1 | 11/2009 | Schuster et al. | |
| 2009/0316141 A1 | 12/2009 | Feldkhun | |
| 2010/0135547 A1 | 6/2010 | Lee et al. | |
| 2010/0271705 A1 | 10/2010 | Hung | |
| 2011/0075928 A1 | 3/2011 | Jeong et al. | |
| 2011/0192976 A1 | 8/2011 | Own et al. | |
| 2011/0235863 A1 | 9/2011 | Maiden | |
| 2012/0069344 A1 | 3/2012 | Liu | |
| 2012/0099803 A1 | 4/2012 | Ozcan et al. | |
| 2012/0105618 A1 | 5/2012 | Brueck et al. | |
| 2012/0118967 A1 | 5/2012 | Gerst | |
| 2012/0157160 A1 | 6/2012 | Ozcan et al. | |
| 2012/0218379 A1 | 8/2012 | Ozcan et al. | |
| 2012/0248292 A1 | 10/2012 | Ozcan et al. | |
| 2012/0250032 A1 | 10/2012 | Wilde et al. | |
| 2012/0281929 A1 | 11/2012 | Brand et al. | |
| 2013/0083886 A1 | 4/2013 | Carmi et al. | |
| 2013/0093871 A1 | 4/2013 | Nowatzyk et al. | |
| 2013/0094077 A1 | 4/2013 | Brueck et al. | |
| 2013/0100525 A1 | 4/2013 | Chiang et al. | |
| 2013/0170767 A1 | 7/2013 | Choudhury et al. | |
| 2013/0182096 A1 | 7/2013 | Boccara et al. | |
| 2013/0223685 A1 | 8/2013 | Maiden | |
| 2014/0007307 A1 | 1/2014 | Routh, Jr. et al. | |
| 2014/0029824 A1 | 1/2014 | Shi et al. | |
| 2014/0043616 A1 | 2/2014 | Maiden et al. | |
| 2014/0050382 A1 | 2/2014 | Adie et al. | |
| 2014/0118529 A1 | 5/2014 | Zheng et al. | |
| 2014/0126691 A1 | 5/2014 | Zheng et al. | |
| 2014/0152801 A1 | 6/2014 | Fine et al. | |
| 2014/0153692 A1 | 6/2014 | Larkin et al. | |
| 2014/0160236 A1 | 6/2014 | Ozcan et al. | |
| 2014/0267674 A1 | 9/2014 | Mertz et al. | |
| 2014/0347672 A1 | 11/2014 | Pavillon et al. | |
| 2014/0368812 A1 | 12/2014 | Humphry et al. | |
| 2015/0036038 A1 | 2/2015 | Horstmeyer et al. | |
| 2015/0054979 A1 | 2/2015 | Ou et al. | |
| 2015/0160450 A1 | 6/2015 | Ou et al. | |
| 2015/0264250 A1 | 9/2015 | Ou et al. | |
| 2015/0331228 A1 | 11/2015 | Horstmeyer et al. | |
| 2016/0088205 A1 | 3/2016 | Horstmeyer et al. | |
| 2016/0178883 A1 | 6/2016 | Horstmeyer et al. | |
| 2016/0202460 A1 | 7/2016 | Zheng | |
| 2016/0210763 A1 | 7/2016 | Horstmeyer et al. | |
| 2016/0216208 A1 | 7/2016 | Kim et al. | |
| 2016/0216503 A1 | 7/2016 | Kim et al. | |
| 2016/0266366 A1 | 9/2016 | Chung et al. | |
| 2016/0320595 A1 | 11/2016 | Horstmeyer et al. | |
| 2016/0320605 A1 | 11/2016 | Ou et al. | |
| 2016/0341945 A1 | 11/2016 | Ou et al. | |
| 2017/0273551 A1 | 9/2017 | Chung et al. | |
| 2017/0299854 A1 | 10/2017 | Kim et al. | |
| 2017/0354329 A1 | 12/2017 | Chung et al. | |
| 2018/0088309 A1 | 3/2018 | Ou et al. | |

FOREIGN PATENT DOCUMENTS

| | | |
|---|---|---|
| CN | 102608597 A | 7/2012 |
| JP | 2007-299604 A | 11/2007 |
| JP | 2010-012222 A | 1/2010 |
| KR | 10-1998-012222 A | 11/1998 |
| WO | 99/53469 A1 | 10/1999 |
| WO | WO 2002/102128 A1 | 12/2002 |
| WO | 03/062744 A1 | 7/2003 |
| WO | 2008/116070 A1 | 9/2008 |
| WO | 2011/093043 A1 | 8/2011 |
| WO | WO 2012/037182 A1 | 3/2012 |
| WO | 2014/070656 A1 | 5/2014 |
| WO | 2015/017730 A1 | 2/2015 |
| WO | 2015/027188 A1 | 2/2015 |
| WO | 2016/090331 | 6/2016 |
| WO | 2016/106379 A1 | 6/2016 |
| WO | 2016/118761 A1 | 7/2016 |
| WO | 2016/123156 A1 | 8/2016 |
| WO | 2016/123157 A1 | 8/2016 |
| WO | 2016/149120 A1 | 9/2016 |
| WO | WO 2016/187591 A1 | 11/2016 |
| WO | WO 2017081539 A1 | 5/2017 |
| WO | WO 2017081540 A1 | 5/2017 |
| WO | WO 2017081542 A2 | 5/2017 |

OTHER PUBLICATIONS

U.S. Notice of Allowance dated Jan. 14, 2016 in U.S. Appl. No. 14/448,850.
U.S. Notice of Allowance dated Jan. 22, 2016 in U.S. Appl. No. 14/466,481.
U.S. Notice of Allowance dated Apr. 13, 2016 in U.S. Appl. No. 14/448,850.
U.S. Notice of Allowance dated Apr. 22, 2016 in U.S. Appl. No. 14/466,481.
U.S. Office Action dated Jul. 14, 2016 in U.S. Appl. No. 15/007,196.

(56) References Cited

OTHER PUBLICATIONS

U.S. Notice of Allowance dated Aug. 23, 2016 in U.S. Appl. No. 14/466,481.
U.S. Office Action dated Aug. 16, 2016 in U.S. Appl. No. 14/065,280.
U.S. Office Action dated Sep. 16, 2016 I U.S. Appl. No. 14/065,305.
U.S. Notice of Allowance dated Nov. 2, 2016 in U.S. Appl. No. 14,572,493.
U.S. Office Action dated Nov. 22, 2016 in U.S. Appl. No. 15/003,559.
International Search Report and Written Opinion dated Feb. 21, 2014 in PCT/US2013/067068.
International Preliminary Report on Patentability dated May 14, 2015 in PCT/US2013/067068.
European Third-Party Observations, dated Jan. 20, 2016 in EP Application No. 13851670.3.
European Extended Search Report dated Mar. 31, 2016 in EP Application No. 13851670.3.
International Preliminary Report on Patentability dated Mar. 3, 2016 issued in PCT/US2014/052351.
International Search Report and Written Opinion dated Dec. 5, 2014 issued in PCT/US2014/052351.
International Search Report and Written Opinion dated Nov. 13, 2014 issued in PCT/US2014/049297.
International Preliminary Report on Patentability dated Feb. 11, 2016 issued in PCT/US2014/049297.
International Search Report and Written Opinion dated Feb. 22, 2016 issued in PCT/US2015/064126.
International Search Report and Written Opinion dated Apr. 19, 2016 issued in PCT/US2015/067498.
International Search Report and Written Opinion dated May 4, 2016 issued in PCT/US2016/015001.
International Search Report and Written Opinion dated May 11, 2016 issued in PCT/US2016/015002.
International Search Report and Written Opinion dated Jun. 27, 2016 issued in PCT/US2016/022116.
International Search Report and Written Opinion dated Jun. 30, 2016 issued in PCT/US2016/014343.
International Search Report and Wrtitten Opinion dated Sep. 5, 2016 issued in PCT/US2016/033638.
Chinese Office Action [Description in English] dated Jul. 11, 2016 issued in Application No. CN 201380068831.6.
"About Molemap," Retrieved Oct. 23, 2015, 2 pages. [http://molemap.net.au/about-us/].
Abramomwitz, M. et al, "Immersion Media," Olympus Microscopy Resource Center, 2012, 6 pp. [http://www.olympusmicro.com/primer/anatomy/immersion.html].
Abramomwitz, M., et al, "Field Curvature," Olympus Microscopy Resource Center, 2012, 3 pp. [http://www.olympusmicro.com/primer/anatomy/fieldcurvature.html].
"Age-Related Macular Degeneration (AMD) | National Eye Institute." [Online]. Available: https://www.nei.nih.gov/eyedata/amd#top. [Accessed: Apr. 5, 2016].
Alexandrov, S., et al, "Spatial information transmission beyond a system's diffraction limit using optical spectral encoding of the spatial frequency," Journal of Optics A: Pure and Applied Optics 10, 025304 (2008).
Alexandrov, S.A., et al, "Synthetic Aperture Fourier holographic optical microscopy," Phys. Rev. Lett. 97, 168102 (2006).
Arimoto, H., et al, "Integral three-dimensional imaging with digital reconstruction," Opt. Lett. 26, 157-159 (2001).
Balan, R., et al, "On signal reconstruction without phase, Applied and Computational Harmonic Analysis 20," No. 3 (2006): 345-356.
Balan, R., et al, "Painless reconstruction from magnitudes of frame coefficients," J Fourier Anal Appl 15:488-501 (2009).
Bauschke, H.H., et al, "Phase retrieval, error reduction algorithm, and Fienup variants: a view from convex optimization," J Opt Soc Am A 19:1334-1345 (2002).

Becker, S., et al, "Templates for convex cone problems with applications to sparse signal recovery," Technical report, Department of Statistics, Stanford University, (2010), 48 Pages.
Betti, R., et al, "Observational study on the mitotic rate and other prognostic factors in cutaneous primary melanoma arising from naevi and from melanoma de novo," Journal of the European Academy of Dermatology and Venereology, 2014.
Bian, L., et al, "Fourier ptychographic reconstruction using Wirtinger flow optimization," Opt. Express 23:4856-4866 (2015).
Bian, Z., et al, "Adaptive system correction for robust Fourier ptychographic imaging," Optics express, 2013. 21(26): p. 32400-32410.
BioTek® Brochure: BioTek's Multi-Mode Microplate Reading Techonologies, 2016, 2 pp. [http://www.biotek.com].
Bishara, W., et al, "Holographic pixel super-resolution in portable lensless on-chip microscopy using a fiber-optic array," Lab Chip 11(7), 1276-1279 (2011).
Bishara, W., et al, "Lensfree on-chip microscopy over a wide field-of-view using pixel super-resolution," Opt. Express 18(11), 11181-11191 (2010).
Blum, A., et al, "Clear differences in hand-held dermoscopes," JDDG: Journal der Deutschen Dermatologischen Gesellschaft, 2006, 4(12): p. 1054-1057.
Blum, A., et al, Dermatoskopie von Hauttumoren: Auflichtmikroskopie; Dermoskopie; digitale Bildanalyse; mit 28 Tabellen. 2003: Springer DE, Chapter 4 "Dermatoskopisch sichtbare Strukturen" p. 15-66.
Born, M., et al, "Principles of Optics: Electromagnetic theory of propagation, interference and diffraction of light" 7th Ed., Cambridge Univ. Press, (1999) pp. 1-31.
Brady, D., et al, "Multiscale gigapixel photography," Nature 486, 386-389 (2012).
Burer, S., et al, "A nonlinear programming algorithm for solving semidefinite programs via low-rank factorization," Math Program, Ser B 95:329-357 (2003).
Burer, S., et al, "Local minima and convergence in low-rank semidefinite programming. Math Program," Ser A 103:427-444 (2005).
Candes, E.J., et al, "Phase retrieval via matrix completion," SIAM J. Imaging Sci. 6:199-225 (2012).
Candes, E.J., et al, "Phase retrieval via Wirtinger flow: theory and algorithms," IEEE Trans. Info. Theory 61:1985-2007 (2015).
Candes, E.J., et al, "PhaseLift: exact and stable signal recovery from magnitude measurements via convex programming.," Comm Pure Appl Math 66:1241-1274 (2013).
Carroll, J., "Adaptive optics retinal imaging: applications for studying retinal degeneration," Arch. Ophthalmol., vol. 126, pp. 857-858, 2008.
Chao, W. et al, "Soft X-ray microscopy at a spatial resolution better than 15 nm," Nature Letters, vol. 435/30, Jun. (2005) pp. 1210-1213.
Chen, T., et al, "Polarization and phase shifting for 3D scanning of translucent objects," Proc. CVPR, (2007).
Chin, L., et al, "Malignant melanoma: genetics and therapeutics in the genomic era," Genes & development, 2006, 20(16): p. 2149-2182.
Choi, W., et al, "Tomographic phase microscopy," Nature Methods 4(9) (2007), pp. 1-3 Published Online Aug. 12, 2007.
Chung, J., et al, "Counting White Blood Cells from a Blood Smear Using Fourier Ptychographic Microscopy," PLoS One 10(7), e0133489 (2015).
Chung, J., et al, "Wide field-of-view fluorescence image deconvolution with aberration-estimation from Fourier ptychography," Feb. 1, 2016, vol. 7, No. 2, Biomedical Optics Express 352.
Colomb, T., et al, "Automatic procedure for aberration compensation in digital holographic microscopy and applications to specimen shape compensation," Appl. Opt. 45, 851-863 (2006).
De Sa, C., et al, "Global convergence of stochastic gradient descent for some non convex matrix problems," Proc. 32nd Int. Conf. Machine Learning (2015), 10 pp.
Debailleul, M., et al, "High-resolution three-dimensional tomographic diffractive microscopy of transparent inorganic and biological samples," Optic Letters 34 (2008).

(56) References Cited

OTHER PUBLICATIONS

Denis, L., et al, "Inline hologram reconstruction with sparsity constraints," Opt. Lett. 34, pp. 3475-3477 (2009).
Di, J., et al, "High resolution digital holographic microscopy with a wide field of view based on a synthetic aperture technique and use of linear CCD scanning," Appl. Opt. 47, pp. 5654-5659 (2008).
Dierolf, M., et al, "Ptychographic coherent diffractive imaging of weakly scattering specimens," New J. Phys. 12, 035017 (2010).
Dierolf, M., et al, "Ptychographic X-ray computed tomography at the nanoscale," Nature, vol. 467, pp. 436-439, (2010).
"Doctor Mole—Skin Cancer App," Retrieved Oct. 23, 2015, 1 page. [http://www.doctormole.com].
Dong, S., et al, "FPscope: a field-portable high-resolution microscope using a cellphone lens," Biomed. Opt. Express 5(10), 3305-3310 (2014).
Dong, S., et al, "High-resolution fluorescence imaging via pattern-illuminated Fourier ptychography," Opt. Express 22(17), 20856-20870 (2014).
Dong, S., et al, "Aperture-scanning Fourier ptychography for 3D refocusing and super-resolution macroscopic imaging," pp. 13586-13599 (Jun. 2, 2014).
Eldar, Y.C., et al, "Sparse phase retrieval from short-time Fourier measurements," IEEE Signal Processing Letters 22, No. 5 (2015): 638-642.
Emile, O., et al, "Rotating polarization imaging in turbid media," Optics Letters 21(20), (1996).
Faulkner, H.M.L., and Rodenburg, J.M., "Error tolerance of an iterative phase retrieval algorithm for moveable illumination microscopy," Ultramicroscopy 103(2), 153-164 (2005).
Faulkner, H.M.L., and Rodenburg, J.M., "Movable aperture lensless transmission microscopy: a novel phase retrieval algorithm," Phys. Rev. Lett. 93, 023903 (2004).
Fazel, M., "Matrix rank minimization with applications," PhD Thesis (Stanford University, Palo Alto, CA). (2002).
Feng, P., et al, "Long-working-distance synthetic aperture Fresnel off-axis digital holography," Optics Express 17, pp. 5473-5480 (2009).
Fienup, J. R., "Invariant error metrics for image reconstruction," Appl. Opt. 36(32), 8352-8357 (1997).
Fienup, J. R., "Lensless coherent imaging by phase retrieval with an illumination pattern constraint," Opt. Express 14, 498-508 (2006).
Fienup, J. R., "Phase retrieval algorithms: a comparison," Appl. Opt. 21, 2758-2769 (1982).
Fienup, J. R., "Reconstruction of a complex-valued object from the modulus of its Fourier transform using a support constraint," J. Opt. Soc. Am. A 4, 118-123 (1987).
Fienup, J. R., "Reconstruction of an object from the modulus of its Fourier transform," Opt. Lett. 3, 27-29 (1978).
Gan, X., et al, "Image enhancement through turbid media under a microscope by use of polarization gating methods," JOSA A 16(9), (1999).
Gerke T.D., et al, "Aperiodic volume optics," Nature Photonics (2010), vol. 4, pp. 188-193.
Ghosh, A., et al, "Multiview face capture using polarized spherical gradient illumination," ACM Transactions on Graphics 30(6) (2011).
Godara, P., et al, "Adaptive optics retinal imaging: emerging clinical applications.," Optom. Vis. Sci., vol. 87, No. 12, pp. 930-941, Dec. 2010.
Goodman, J.W., "Introduction to Fourier Optics," Roberts & Company Publication, Third Edition, chapters 1-6, pp. 1-172 (2005).
Goodson, A.G., et al, "Comparative analysis of total body and dermatoscopic photographic monitoring of nevi in similar patient populations at risk for cutaneous melanoma," Dermatologic Surgery, 2010. 36(7): p. 1087-1098.
Granero, L., et al, "Synthetic aperture superresolved microscopy in digital lensless Fourier holography by time and angular multiplexing of the object information," Appl. Opt. 49, pp. 845-857 (2010).

Grant, M., et al, "CVX: Matlab software for disciplined convex programming," version 2.0 beta. http://cvxr.com/cvx, (Sep. 2013), 3 pages.
Greenbaum, A., et al, "Field-portable wide-field microscopy of dense samples using multi-height pixel super resolution based lensfree imaging," Lab Chip 12(7), 1242-1245 (2012).
Greenbaum, A., et al, "Increased space-bandwidth product in pixel super-resolved lensfree on-chip microscopy," Sci. Rep. 3, p. 1717 (2013).
Gruev, V., et al, "Dual-tier thin film polymer polarization imaging sensor," Optics Express, vol. 18, No. 18, 12 pages. (2010).
Guizar-Sicairos, M., and Fienup, J.R.,"Phase retrieval with transverse translation diversity: a nonlinear optimization approach," Opt. Express 16, 7264-7278 (2008).
Gunturk, B.K., et al, "Image Restoration: Fundamentals and Advances," vol. 7, Chapter 3, pp. 63-68 (CRC Press, 2012).
Gustafsson, M.G.L., "Surpassing the lateral resolution limit by a factor of two using structured illumination microscopy," J. Microsc. 198, 82-87 (2000).
Gutzler, T., et al, "Coherent aperture-synthesis, wide-field, high-resolution holographic microscopy of biological tissue," Opt. Lett. 35, pp. 1136-1138 (2010).
Haigh, S. J., et al, (2009) "Atomic structure imaging beyond conventional resolution limits in the transmission electron microscope"; Physical Review Letters 103. 126101-1 126101-4.
Han, C., et al, "Wide Field-of-View On-Chip Talbot Fluorescence Microscopy for Longitudinal Cell Culture Monitoring from within the Incubator" Anal. Chem. 85(4), 2356-2360 (2013).
Hillman, T.R., et al, "High-resolution, wide-field object reconstruction with synthetic aperture Fourier holographic optical microscopy," Opt. Express 17, pp. 7873-7892 (2009).
Hofer, H., et al, "Dynamics of the eye's wave aberration," J. Opt. Soc. Am. A, vol. 18, No. 3, p. 497, 2001.
Hofer, H., et al, "Organization of the human trichromatic cone mosaic.," J. Neurosci., vol. 25, No. 42, pp. 9669-9679, Oct. 2005.
Hong, S-H., et al, "Three-dimensional volumetric object reconstruction using computational integral imaging," Opt. Express 12, 483-491 (2004).
Hoppe, W., "Diffraction in inhomogeneous primary wave fields. 1. Principle of phase determination from electron diffraction interference," Acta Crystallogr. A25, 495-501 1969.
Horstmeyer, R., et al, "A phase space model of Fourier ptychographic microscopy," Optics Express, 2014. 22(1): p. 338-358.
Horstmeyer, R., et al, "Digital pathology with fourier ptychography," Comput. Med. Imaging Graphics 42, 38-43 (2015).
Horstmeyer, R., et al, "Overlapped fourier coding for optical aberration removal," Manuscript in preparation, 19 pages (2014).
Horstmeyer, R., et a1, "Solving ptychography with a convex relaxation," Physics Optics (2014) 1-8 pages.
Hue, F., et al, "Wave-front phase retrieval in transmission electron microscopy via ptychography," Phys. Rev. B 82, 121415 (2010).
Humphry, M., et al, "Ptychographic electron microscopy using high-angle dark-field scattering for sub-nanometre resolution imaging," Nat. Commun. 3, 730 (2012).
IncuCyte® ZOOM System, Brochure, 1-4 pp. (2016) (retrieved Feb. 25, 2016), [http://www.essenbioscience.com/media/uploads/files/8000-0333-E00-IncuCyte_ZOOM_brochure.pdf].
Jaganathan, K., et al, "Recovery of sparse 1-D signals from the magnitudes of their Fourier transform," IEEE International Symposium on Information Theory Proceedings (2012): 1473-1477.
Jaganathan, K., et al, "Phase retrieval with masks using convex optimization," IEEE International Symposium on Information Theory Proceedings (2015): 1655-1659.
Jaganathan, K., et al, "STFT Phase retrieval: uniqueness guarantees and recovery algorithms," arXiv preprint arXiv:1508.02820 (2015).
Joeres, S., et al, "Retinal imaging with adaptive optics scanning laser ophthalmoscopy in unexplained central ring scotoma.," Arch. Ophthalmol., vol. 126, No. 4, pp. 543-547, Apr. 2008.
Jung, J.H., et al, "Microfluidic-integrated laser-controlled microactuators with on-chip microscopy imaging functionality," Lab Chip 14 (19), Oct. 7, 2014, pp. 3781-3789.

(56) References Cited

OTHER PUBLICATIONS

Kay, D. B., et al, "Outer retinal structure in best vitelliform macular dystrophy.," JAMA Ophthalmol., vol. 131, pp. 1207-1215, 2013.
Kim, J., et al, Incubator embedded cell culture imaging system (EmSight) based on Fourier ptychographic microscopy. EmSight manuscript, Optical Society of America, 2015.
Kim, M., et al, "High-speed synthetic aperture microscopy for live cell imaging," Opt. Lett. 36, pp. 148-150 (2011).
Kirkland, A.I., et al, "Multiple beam tilt microscopy for super resolved imaging;" Japanese Society of Electron Microscopy: Journal of Electron Microscopy I: 11-22(1997), vol. 46, No. 1 1997.
Kirkland, A.I., et al, "Super-resolution by aperture synthesis: tilt series reconstruction in CTEM," Ultramicroscopy 57, (1995) 355-374, Received May 27, 1994, in final form Oct. 2, 1994; 1995 Elsevier Science B.V. SSDI 0304-3991(94)00191-x.
Kittler, H., et al, "Morphologic changes of pigmented skin lesions: a useful extension of the ABCD rule for dermatoscopy," Journal of the American Academy of Dermatology, 1999. 40(4): p. 558-562.
Kozak, I., "Retinal imaging using adaptive optics technology.," Saudi J. Ophthalmol. Off. J. Saudi Ophthalmol. Soc., vol. 28, No. 2, pp. 117-122, Apr. 2014.
Lauer, V., "New Approach to optical diffraction tomography yielding a vector equation of diffraction tomography and a novel tomography microscope," Journal of Microscopy, vol. 205, Pt 2 Feb. 2002, pp. 165-176, The Royal Microscopical Society 2001.
Lee, K., et al, "Synthetic Fourier transform light scattering," Optics Express 21 (2013).
Levoy, M., et al, "Light field microscopy," ACM Trans. Graphics 25, (2006).
Levoy, M., et al, "Recording and controlling the 4D light field in a microscope using microlens arrays," J. Microsc. 235 (2009).
Li, X., et al, "Sparse signal recovery from quadratic measurements via convex programming," SIAM Journal on Mathematical Analysis 45, No. 5 (2013): 3019-3033.
Lohmann, A. W., et al, "Space-bandwidth product of optical signals and systems," J. Opt. Soc. Am. A 13, pp. 470-473 (1996).
Lue, N., et al, "Live Cell Refractometry Using Hilbert Phase Microscopy and Confocal Reflectance Microscopy," The Journal of Physical Chemistry A, 113, pp. 13327-13330 (2009).
LUXEXCEL® Brochure, LUXEXCEL: 3D Printing Service Description, Retrieved Mar. 7, 2016, 5 pp. [http://www.luxexcel.com].
"Lytro," Retrieved Oct. 23, 2015, 6 pp. [hups://www.lytro.com/].
Ma, W., et al, "Rapid Acquisition of Specular and Diffuse Normal Maps from Polarized Spherical Gradient Illumination," University of Southern California, Institute for Creative Technologies, 12 pages (2007).
Mahajan, V. N., "Zernike circle polynomials and optical aberrations of systems with circular pupils," Appl. Opt. 33(34), 8121-8124 (1994).
Maiden, A. M., et al, "A new method of high resolution, quantitative phase scanning microscopy," in: M.T. Postek, D.E. Newbury, S.F. Platek, D.C. Joy (Eds.), SPIE Proceedings of Scanning Microscopy, 7729, 2010.
Maiden, A. M., et al, "An improved ptychographical phase retrieval algorithm for diffractive imaging," Ultramicroscopy 109(10), 1256-1262 (2009).
Maiden, S. M., et al, "Superresolution imaging via ptychography," Journal of the Optical Society of America A. Apr. 2011, vol. 28 No. 4, pp. 604-612.
Maiden, A. M., et al, "Optical ptychography: a practical implementation with useful resolution," Opt. Lett. 35, 2585-2587 (2010).
Marchesini S., "A unified evaluation of iterative projection algorithms for phase retrieval," Rev Sci Instrum 78:011301 (2007).
Marchesini S., et al, "Augmented projections for ptychographic imaging," Inverse Probl 29:115009 (2013).
Marrison, J., et al, "Ptychography—a label free, high-contrast imaging technique for live cells using quantitative phase information," Sci. Rep. 3, 2369 (2013).
Medoff, B.P., et al, "Iterative convolution backprojection algorithms for image reconstruction from limited data," J. Opt. Soc. Am. vol. 73, No. 11, Nov. 1983, pp. 1493-1500.
"Melafind," Retrieved Oct. 23, 2015, 4 pages. [http://www.melafind.com/].
Meyer, R.R., et al, "A method for the determination of the wave aberration function of high-resolution TEM," Ultramicroscopy 99 (2004) 115-123: Elsevier B.V. Doi: 10.1016/j.ultramic.2003.11.001.
Miao, J., et al, "High Resolution 3D X-Ray Diffraction Microscopy," Physical Review Letters, Aug. 19, 2002, vol. 89, No. 8, pp. 1-4.
Mico, V., et al, "Synthetic aperture microscopy using off-axis illumination and polarization coding," Optics Communications, pp. 276, 209-217 (2007).
Mico, V., et al, "Synthetic aperture superresolution with multiple off-axis holograms," JOSA A 23, pp. 3162-3170 (2006).
Mir, M. et al, "Optical measurement of cycle-dependent cell growth," Proceedings of the National Academy of Sciences 108, pp. 13124-13129 (2011).
Mir, M., et al, "Blood screening using diffraction phase cytometry," Journal of Biomedical Optics 15, pp. 027016-027014 (2010).
Moreno, I., "Creating a desired lighting pattern with an LED array," 8th International Conference on Solid State Lighting, Proceedings of SPIE, vol. 7058, 2008, 9 pp.
Mrejen, S., et al, "Adaptive optics imaging of cone mosaic abnormalities in acute macular neuroretinopathy.," Ophthalmic Surg. Lasers Imaging Retina, vol. 45, No. 6, pp. 562-569, Jan. 2014.
Nayar, S. K., et al, "Fast separation of direct and global components of a scene using high frequency illumination," ACM Transactions on Graphics 25(3) (2006).
Ng, R., et al, "Light field photography with a hand-held plenoptic camera", Computer Science Technical Report CSTR, 2005. 2(11).
Nomura, H., and Sato, T., "Techniques for measuring aberrations in lenses used in photolithography with printed patterns," Appl. Opt. 38(13), 2800-2807 (1999).
Ohlsson, H., et al, "Compressive phase retrieval from squared output measurements via semidefinite programming," arXiv:1111.6323 (2011).
Ou, X., et al, "High numerical aperture Fourier ptychography: principle, implementation and characterization," Opt. Express 23:3472-3491 (2015).
Ou, X., et al, "Quantitative phase imaging via Fourier ptychographic microscopy," Optics Letters, 2013. 38(22): p. 4845-4848.
Ou. X., et al, "Embedded pupil function recovery for Fourier ptychographic microscopy," Optics Express 22 (5), pp. 4960-4972 (2014), with Erratum (2015).
Ou. X., et al, "Embedded pupil function recovery for Fourier ptychographic microscopy," submitted Dec. 26, 2013; 13 pp.
Pacheco, S., et al, "Reflective Fourier Ptychography," J. Biomed. Opt. 21(2), pp. 026010-1-026010-7, (Feb. 18, 2016). [http://biomedicaloptics.spiedigitallibrary.org].
Recht, B., et al, "Guaranteed minimum-rank solutions of linear matrix equations via nuclear norm minimization," SIAM Review 52, No. 3 (2010): 471-501.
Reinhard, E., et al, "High Dynamic Range Imaging: Acquisition, Display, and Image-based Lighting" (Morgan Kaufmann, 2010).
Rodenburg, J. M., et al, "A phase retrieval algorithm for shifting illumination," Appl. Phys. Lett. 85, 4795-4797 (2004).
Rodenburg, J. M., et al, "Hard-X-ray lensless imaging of extended objects," Phys. Rev. Lett. 98, 034801 (2007).
Rodenburg, J. M., et al, "The theory of super-resolution electron microscopy via Wigner-distribution deconvolution," Phil. Trans. R. Soc. Lond. A 339, 521-553 (1992).
Rodenburg, J., "Ptychography and related diffractive imaging methods," Adv Imaging Electron Phys.150, 87-184 (2008).
Rossi, E.A., et al, "In vivo imaging of retinal pigment epithelium cells in age related macular degeneration.," Biomed. Opt. Express, vol. 4, No. 11, pp. 2527-2539, Jan. 2013.
Rowe, M., et al, "Polarization-difference imaging: a biologically inspired technique for observation through scattering media," Optics Letters, vol. 20, No. 6, 3 pages (1995).

(56) References Cited

OTHER PUBLICATIONS

Schechner, Y., "Multiplexing for Optimal Lighting," IEEE Transactions on Pattern Analysis and Machine Intelligence, vol. 29, No. 8, 1339-1354 (2007).
Schnars, U., et al, "Digital recording and numerical reconstruction of holograms," Measurement Science and Technology, 13, R85 (2002).
Schwarz, C., et al, "Imaging interferometric microscopy," Optics letters 28, pp. 1424-1426 (2003).
Shechner, Y., et al, "Polarization-based vision through haze," Applied Optics 42(3), (2003).
Shechtman, Y., et al, "Sparsity based sub-wavelength imaging with partially incoherent light via quadratic compressed sensing," Opt Express 19:14807-14822 (2011).
Siegel, R., et al, "Cancer statistics 2013," CA: a cancer journal for clinicians, 2013. 63(1): p. 11-30.
Stoecker, W., et al, "Diagnostic Inaccuracy of Smartphone Applications for Melanoma Detection: Representative Lesion Sets and the Role for Adjunctive Technologies," JAMA Dermatology, 2013. 149(7): p. 884.
Sun, D., et al, "Estimating a signal from a magnitude spectrogram via convex optimization," arXiv:1209.2076 (2012).
Sun, J., et al, "Coded multi-angular illumination for Fourier ptychography based on Hadamard codes," 5 pages (2015).
Tam, K., et al, "Tomographical imaging with limited-angle input," J. Opt. Soc. Am. 21 (1981).
"TFOCS: Templates for First-Order Conic Solvers," CVX Research, CVX Forum, http://cvxr.com/tfocs/.
Thibault, P. et al, "Probe retrieval in ptychographic coherent diffractive imaging," Ultramicroscopy 109(4), 338-343 (2009).
Thibault, P., et al, "High-resolution scanning X-ray diffraction microscopy," Science 321, 2008, pp. 379-382.
Thomas, L., et al, "Semiological value of ABCDE criteria in the diagnosis of cutaneous pigmented tumors," Dermatology, 1998. 197(1): p. 11-17.
Tian, L., et al, "Multiplexed Coded Illumination for Fourier Ptychography with an LED Array Microscope," Optical Society of America, 14 pages (2014).
Tippie, A.E., et al, "High-resolution synthetic-aperture digital holography with digital phase and pupil correction," Opt. Express 19, pp. 12027-12038 (2011).
Turpin, T., et al, "Theory of the synthetic aperture microscope," pp. 230-240 (1995).
Tyson, R., "Principles of Adaptive Optics" (CRC Press, 2010).
Vulovic, M., et al, "When to use the projection assumption and the weak-phase object approximation in phase contrast cryo-EM," Ultramicroscopy 136 (2014) 61-66.
Waldspurger, I., et al, "Phase recovery, maxcut and complex semidefinite programming," Mathematical Programming 149, No. 1-2 (2015): 47-81.
Wang, Q., et al, "Adaptive Optics Microperimetry and OCT Images Show Preserved Function and Recovery of Cone Visibility in Macular Telangiectasia Type 2 Retinal Lesions," Invest. Ophthalmol. Vis. Sci., vol. 56, pp. 778-786 (2015).
Wang, Z., et al, "Tissue refractive index as marker of disease," Journal of Biomedical Optics 16, 116017-116017 (2011).
Watanabe, M., et al, "Telecentric optics for focus analysis," IEEE trans. pattern. anal. mach. intell., 19 1360-1365 (1997).
Wesner, J., et al, "Reconstructing the pupil function of microscope objectives from the intensity PSF," in Current Developments in Lens Design and Optical Engineering III, R. E. Fischer, W. J. Smith, and R. B. Johnson, eds., Proc. SPIE 4767, 32-43 (2002).
Williams, A., et al, "Fourier ptychographic microscopy for filtration-based circulating tumor cell enumeration and analysis," J. Biomed. Opt. 19(6), 066007 (2014).
Wolf, J., et al, "Diagnostic Inaccuracy of Smartphone Applications for Melanoma Detection," JAMA Dermatology, 2013, 149(7): p. 885-885.
Wu, J., et al, "Focal plane tuning in wide-field-of-view microscope with Talbot pattern illumination," Opt. Lett. 36, 2179-2181 (2011).
Wu, J., et al, "Wide field-of-view microscope based on holographic focus grid illumination," Opt. Lett. 35, 2188-2190 (2010).
Xu, W., et al, "Digital in-line holography for biological applications," Proc. Natl Acad. Sci. USA 98, pp. 11301-11305 (2001).
Yuan, C., et al, "Angular multiplexing in pulsed digital holography for aperture synthesis," Optics Letters 33, pp. 2356-2358 (2008).
Zeiss, C., "Microscopy, Cells Need the Perfect Climate, System Solutions for Live Cell Imaging under Physiological Conditions," printed Feb. 2008, 1-42 pgs.
Zhang, Y., et al, "Self-learning based fourier ptychographic microscopy," Optics Express, 16pgs (2015).
Zhang, Y., et al, "Photoreceptor Perturbation Around Subretinal Drusenoid Deposits as Revealed by Adaptive Optics Scanning Laser Ophthalmoscopy," Am. J. Ophthalmol., vol. 158, No. 3, pp. 584-596, 2014.
Zheng, G., et al, "Characterization of spatially varying aberrations for wide field-of-view microscopy," Opt. Express 21, 15131-15143 (2013).
Zheng, G., et al, "Microscopy refocusing and dark-field imaging by using a simple LED array," Opt. Lett. 36, 3987-3989 (2011).
Zheng, G., et al, "0.5 gigapixel microscopy using a flatbed scanner," Biomed. Opt. Express 5, 1-8 (2014).
Zheng, G., et al, "Sub-pixel resolving optofluidic microscope for on-chip cell imaging," Lab Chip 10, pp. 3125-3129 (2010).
Zheng, G. "The ePetri dish, an on-chip cell imaging platform based on subpixel perspective sweeping microscopy (SPSM)," Proc. Natl. Acad. Sci. USA 108, pp. 16889-16894 (2011).
Zheng, G., et al, "Wide-field, high-resolution Fourier ptychographic microscopy," Nature Photonics, vol. 7, pp. 739-745, Published Online Jul. 28, 2013 at www.nature.com/naturephotonics.
Chung, J., et al, "Wide-field Fourier ptychographic microscopy using laser illumination source," Optical Society of America, 13 pgs., Mar. 23, 2016.
Guo, K., et al, "Optimization of sampling pattern and the design of Fourier ptychographic illuminator," Optical Society of America; Optics Express, vol. 23, No. 5, pp. 6171-6180 (2015).
Phillips, Z., et al, "Multi-Contrast Imaging and Digital Refocusing on a Mobile Microscope with a Domed LED Array," PLoS One, 10 (5), pp. 1-13 (2015).
Horstmeyer, R., et al, "Standardizing the resolution claims for coherent microscopy," Nature Photonics, vol. 10, pp. 68-71, Feb. 2016.
Horstmeyer, R., et al, "Solving ptychography with a convex relaxation," New Journal of Physics, vol. 17 (2015) 1-14 pages.
Hoppe, W., "Diffraction in inhomogeneous primary wave fields. 1. Principle of phase determination from electron diffraction interference." Acta Crystallographica Section a-Crystal Physics Diffraction Theoretical and General Crystallography, A25, Jan. 1, 1969, pp. 495-501. (English Machine Translation Incl.).
Reinhard, E., et al, "High Dynamic Range Imaging: Acquisition, Display, and Image-based Lighting" Second Edition § 5.2 HDR Image Capture: Morgan Kaufmann, May 28, 2010, pp. 148-151. <ISBN: 9780123749147>.
Preliminary Amendment dated Mar. 17, 2014 filed in U.S. Appl. No. 14/065,280.
Preliminary Amendment dated Apr. 25, 2016 filed in U.S. Appl. No. 14/710,947.
Preliminary Amendment dated Mar. 17, 2014 filed in U.S. Appl. No. 14/065,305.
Preliminary Amendment dated Nov. 28, 2016 filed in U.S. Appl. No. 15/209,604.
U.S. Supplemental Notice of Allowance dated Dec. 12, 2016 in U.S. Appl. No. 14/572,493.
U.S. Notice of Allowance dated Jan. 13, 2017 in U.S. Appl. No. 14/065,305.
U.S. Final Office Action dated Jan. 23, 2017 in U.S. Appl. No. 15/007,196.
U.S. Office Action dated Feb. 21, 2017 in U.S. Appl. No. 14/960,252.
U.S. Supplemental Notice of Allowability dated Mar. 2, 2017 in U.S. Appl. No. 14/065,305.
U.S. Notice of Allowance dated Mar. 8, 2017 in U.S. Appl. No. 14/572,493.

(56) References Cited

OTHER PUBLICATIONS

U.S. Office Action dated Mar. 13, 2017 in U.S. Appl. No. 14/658,019.
U.S. Notice of Allowance dated Mar. 22, 2017 in U.S. Appl. No. 15/007,196.
U.S. Office Action dated Mar. 24, 2017 in U.S. Appl. No. 14/710,947.
U.S. Notice of Allowance dated Mar. 31, 2017 in U.S. Appl. No. 14/572,493.
U.S. Final Office Action dated Apr. 3, 2017 in U.S. Appl. No. 14/065,280.
U.S. Notice of Allowance dated Jun. 9, 2017 in U.S. Appl. No. 14/065,305.
U.S. Notice of Allowance dated Jun. 9, 2017 in U.S. Appl. No. 15/007,196.
U.S. Notice of Allowance dated Jun. 20, 2017 in U.S. Appl. No. 14/572,493.
U.S. Final Office Action dated Jul. 27, 2017 in U.S. Appl. No. 15/003,559.
Chinese Office Action [Description in English] dated Dec. 13, 2016 issued in Application No. CN201480057911.6.
Extended European Search Report dated Feb. 16, 2017 issued in Application No. 14837844.1.
Extended European Search Report dated Feb. 15, 2017 issued in Application No. 14832857.8.
Chinese Second Office Action [Description in English] dated Feb. 17, 2017 issued in Application No. CN201380068831.6.
International Preliminary Report on Patentability dated Jun. 15, 2017 issued in Application No. PCT/US2015/064126.
European Office Action dated May 16, 2017 issued in European Patent Application No. 13851670.3.
International Preliminary Report on Patentability dated Jul. 6, 2017 issued in Application No. PCT/US2015/067498.
International Preliminary Report on Patentability dated Aug. 3, 2017 issued in Application No. PCT/US2016/014343.
International Preliminary Report on Patentability dated Aug. 10, 2017 issued in Application No. PCT/US2016/015001.
Bian, L., et al, "Fourier ptychographic reconstruction using Poisson maximum likelihood and truncated Wirtinger gradient," Nature Publishing Group; Scientific Reports, vol. 6, No. 27384, Jun. 10, 2016, pp. 1-10. <doi: 10.1038/srep27384>.
Bunk, O., et al, "Influence of the overlap parameter on the convergence of the ptychographical iterative engine," Ultramicroscopy, vol. 108, (2008), pp. 481-487. <doi:10.1016/j.ultramic.2007.08.003>.
Chai, A., et al, "Array imaging using intensity-only measurements," IOP Publishing: Inverse Problems, vol. 27, No. 1, Jan. 2011, pp. 1-16. <doi:10.1088/0266-5611/27/1/015005>.
Horstmeyer, R., et al, "Diffraction tomography with Fourier ptychography," Optica, Optical Society of America, vol. 3, No. 8, Aug. 2016, pp. 827-835. <doi:10.1364/OPTICA.3.000827>.
Kawata, S. et al, "Optical microscope tomography. I. Support constraint," Journal Optical Society America A, vol. 4, No. 1, Jan. 1987, pp. 292-297. <doi:10.1364/JOSAA.4.000292>.
Kim, M., et al, "High-speed synthetic aperture microscopy for live cell imaging," Optics Letters, vol. 36, No. 2, Jan. 15, 2011, pp. 148-150. <doi:10.1364/OL.36.000148>.
Lu, H., et al, "Quantitative phase imaging and complex field reconstruction by pupil modulation differential phase contrast," Optics Express, vol. 24, No. 22, Oct. 31, 2016, pp. 25345-25361. <doi:10.1364/OE.24.025345>.
Ou, X., et al, "Aperture scanning Fourier ptychographic microscopy," Biomedical Optics Express, vol. 7, No. 8, Aug. 1, 2016, pp. 3140-3150. <doi:10.1364/BOE.7.003140>.
Tian, L., et al, "3D differential phase-contrast microscopy with computational illumination using an LED array," Optics Letters, vol. 39, No. 5, Mar. 1, 2014, pp. 1326-1329. <doi:10.1364/OL39.001326>.
Tian, L., et al, "Computational illumination for high-speed in vitro Fourier ptychographic microscropy," Optica: Research Article, vol. 2, No. 10, Oct. 14, 2015, pp. 904-911. <doi:10.1364/OPTICA.2.000904>.
Wu, J., et al, "Harmonically matched grating-based full-field quantitative high-resolution phase microscope for observing dynamics of transparent biological samples," Optics Express, vol. 15, No. 26, Dec. 24, 2007, pp. 18141-18155. <doi:10.1364/OE.15.018141>.
Wu, J., et al, "Paired-angle-rotation scanning optical coherence tomography forward-imaging probe," Optics Letters, vol. 31, No. 9, May 1, 2006, pp. 1265-1267. <doi:10.1364/OL.31.001265>.
Yeh, et al., "Experimental robustness of Fourier ptychography phase retrieval algorithms," Optics Express, vol. 23, No. 26, Dec. 28, 2015, pp. 33214-33240. <doi: 10.1364/OE.23.033214>.
Zheng, G., "Fourier Ptychographic Imaging: A MATLAB tutorial," IOP Concise Physics, Morgan & Claypool Publication, San Rafael, CA., May 2016, pp. 96. <ISBN: 978-1-6817-4272-4 (ebook)> <doi: 10.1088/978-1-6817-4273-1>.
U.S. Appl. No. 15/620,674, filed Jun. 12, 2017, Chung, J. et al.
U.S. Appl. No. 15/636,494, filed Jun. 28, 2017, Kim, J. et al.
Notice of Allowance dated Dec. 4, 2017 in U.S. Appl. No. 14/065,305.
Final Office Action dated Dec. 14, 2017 in U.S. Appl. No. 14/960,252.
Final Office Action dated Dec. 28, 2017 in U.S. Appl. No. 14/710,947.
Supplemental Notice of Allowance dated Dec. 29, 2017 in U.S. Appl. No. 14/065,305.
U.S. Appl. No. 15/820,295, filed Nov. 21, 2017, Ou.
Chinese Office Action [Description in English] dated May 31, 2016 issued in Application No. CN 201380068831.6.
Chinese Second Office Action [Description in English] dated Jan. 22, 2017 issued in Application No. CN201380068831.6.
U.S. Notice of Allowance dated Aug. 16, 2017 in U.S. Appl. No. 15/209,604.
Office Action dated Aug. 31, 2017 in U.S. Appl. No. 15/636,494.
Office Action dated May 19, 2017 in U.S. Appl. No. 15/081,659.
Notice of Allowance dated Sep. 20, 2017 in U.S. Appl. No. 15/007,196.
Notice of Allowance dated Oct. 11, 2017 in U.S. Appl. No. 14/572,493.
Notive of Allowance dated Oct. 20, 2017 in U.S. Appl. No. 15/081,659.
Office Action dated Nov. 3, 2017 in U.S. Appl. No. 15/068,389.
Office Action dated Nov. 30, 2017 in U.S. Appl. No. 15/007,159.
International Preliminary Report on Patentability dated Aug. 10, 2017 issued in Application No. PCT/US2016/015002.
Chinese Third Office Action [Summary in English] dated Jul. 24, 2017 issued in Application No. 201380068831.6.
Chinese First Office Action [Summary in English] dated Aug. 2, 2017 issued in Application No. CN 201480054301.0.
Australian Office Action dated Sep. 18, 2017 issued in Application No. AU 2014296034.
International Preliminary Report on Patentability dated Sep. 28, 2017 issued in Application No. PCT/US2016/022116.
Japanese Office Action dated Oct. 17, 2017 issued in Application No. 2015-539884.
Chinese Office Action [Summary in English] dated Oct. 26, 2017 issued in CN 201480057911.6.
International Preliminary Report on Patentability dated Nov. 30, 2017 issued in PCT/US2016/033638.
Abrahamsson, S., et al., "Fast multicolor 3D imaging using aberration-corrected mulitfocus microscopy," Brief Communications: Nature Methods, vol. 10, No. 1, Jan. 2013, pp. 60-65. <doi:10.1038/nmeth.2277>.
Kner, P., "Phase diversity for three-dimensional imaging," Journal of the Optical Society of America A, vol. 30, No. 10, Oct. 1, 2013, pp. 1980-1987. <doi:10.1364/JOSAA.30.001980>.
Sankaranarayanan, Aswin C., et al, "CS-MUVI: Video Compressive Sensing for Spatial-Multiplexing Cameras," Proceedings of the IEEE International Conference Computational Photography (ICCP), Apr. 2012, pp. 11. <doi:10.1109/ICCPhot.2012.6215212>.

(56) References Cited

OTHER PUBLICATIONS

Zheng, G., et al, "Wide-field, high-resolution Fourier ptychographic microscopy," Nature Photonics, vol. 7, Sep. 2013, Published Online Jul. 28, 2013, pp. 739-746. <doi:10.1038/NPHOTON.2013.187>.

Wills, S., "Synthetic Apertures for the Optical Domain," Optics & Photonics News Article [webpage], The Optical Society (OSA), Apr. 18, 2017, pp. 2. <URL:https://www.osa-opn.org/home/news-room/2017/april/synthetic_apertures_for_the_optical_domain/>.

Holloway, J., et al. "SAVI: Synthetic apertures for long-range, subdiffraction-limited visible imaging using Fourier ptychography," Science Advances | Research Article, vol. 3, No. 4, Apr. 14, 2017, pp. 1-11. <doi:10.1126/sciadv.1602564> [retrieved on Nov. 28, 2017] <URL:http://advances.sciencemag.org/>.

Final Office Action dated Jan. 17, 2018 in U.S. Appl. No. 14/658,019.

Australian Examination Report 1/Office Action dated Jan. 18, 2018 issued in AU 2014308673.

Office Action dated Jan. 25, 2018 in U.S. Appl. No. 14/065,280.

Notice of Allowance dated Jan. 26, 2018 in U.S. Appl. No. 15/209,604.

Notice of Allowance dated Feb. 9, 2018 in U.S. Appl. No. 15/081,659.

Chinese First Office Action [no english translation] dated Feb. 24, 2018 issued in CN 201680003937.1.

Office Action dated Apr. 4, 2018 issued in U.S. Appl. No. 15/003,559.

Office Action dated Apr. 13, 2018 issued in U.S. Appl. No. 15/160,941.

\* cited by examiner

APERTURE SCANNING FOURIER PTYCHOGRAPHIC IMAGING

CROSS-REFERENCES TO RELATED APPLICATIONS

This application is a continuation of U.S. patent application Ser. No. 14/448,850, titled "Aperture Scanning Fourier Ptychographic Imaging" and filed on Jul. 31, 2014, which claims benefit of U.S. Provisional Patent Application No. 61/860,786, titled "Generalized Ptychographic Imaging with Optical Transfer Function Modulation" and filed on Jul. 31, 2013 and U.S. Provisional Patent Application No. 61/868,967, titled "Alternative Optical Implementations for Fourier Ptychographic Microscopy" and filed on Aug. 22, 2013; all of these applications are hereby incorporated by reference in their entireties and for all purposes.

STATEMENT AS TO RIGHTS TO INVENTIONS MADE UNDER FEDERALLY SPONSORED RESEARCH OR DEVELOPMENT

This invention was made with government support under Grant No. OD007307 awarded by the National Institutes of Health. The government has certain rights in the invention.

BACKGROUND OF THE INVENTION

Certain embodiments described herein generally relate to imaging techniques, and more specifically to methods, devices, and systems for Fourier ptychographic imaging.

Imaging lenses ranging from microscope objectives to satellite-based cameras are physically limited in the total number of features they can resolve. These limitations are a function of the point-spread function (PSF) size of the imaging system and the inherent aberrations across its image plane field of view (FOV). Referred to as the space-bandwidth product, the physical limitation scales with the dimensions of the lens but is usually on the order of 10 megapixels regardless of the magnification factor or numerical aperture (NA). A discussion of space-bandwidth product of conventional imaging systems can be found in Lohmann, A. W., Dorsch, R. G., Mendlovic, D., Zalevsky, Z. & Ferreira, C., "Space-bandwidth product of optical signals and systems," J. Opt. Soc. Am. A. 13, pages 470-473 (1996), which is hereby incorporated by reference for this discussion. While conventional imaging systems may be able to resolve up to 10 megapixels, there is typically a tradeoff between PSF and FOV. For example, certain conventional microscope objectives can offer a sharp PSF (e.g., 0.5 µm) across a narrow FOV (e.g., 1 mm), while others imaging systems with wide-angle lenses can offer a wide FOV (e.g., 10 mm) at the expense of a blurry PSF (e.g., 5 µm).

Certain interferometric synthetic aperture techniques that try to increase spatial-bandwidth product are described in Di, J. et al., "High resolution digital holographic microscopy with a wide field of view based on a synthetic aperture technique and use of linear CCD scanning," Appl. Opt. 47, pp. 5654-5659 (2008); Hillman, T. R., Gutzler, T., Alexandrov, S. A., and Sampson, D. D., "High-resolution, wide-field object reconstruction with synthetic aperture Fourier holographic optical microscopy," Opt. Express 17, pp. 7873-7892 (2009); Granero, L., Mico, V., Zalevsky, Z., and Garcia, J., "Synthetic aperture superresolved microscopy in digital lensless Fourier holography by time and angular multiplexing of the object information," Appl. Opt. 49, pp. 845-857 (2010); Kim, M. et al., "High-speed synthetic aperture microscopy for live cell imaging," Opt. Lett. 36, pp. 148-150 (2011); Turpin, T., Gesell, L., Lapides, J., and Price, C., "Theory of the synthetic aperture microscope," pp. 230-240; Schwarz, C. J., Kuznetsova, Y., and Brueck, S., "Imaging interferometric microscopy," Optics letters 28, pp. 1424-1426 (2003); Feng, P., Wen, X., and Lu, R., "Long-working-distance synthetic aperture Fresnel off-axis digital holography," Optics Express 17, pp. 5473-5480 (2009); Mico, V., Zalevsky, Z., Garcia-Martinez, P., and Garcia, J., "Synthetic aperture superresolution with multiple off-axis holograms," JOSA A 23, pp. 3162-3170 (2006); Yuan, C., Zhai, H., and Liu, H., "Angular multiplexing in pulsed digital holography for aperture synthesis," Optics Letters 33, pp. 2356-2358 (2008); Mico, V., Zalevsky, Z., and Garcia, J., "Synthetic aperture microscopy using off-axis illumination and polarization coding," Optics Communications, pp. 276, 209-217 (2007); Alexandrov, S., and Sampson, D., "Spatial information transmission beyond a system's diffraction limit using optical spectral encoding of the spatial frequency," Journal of Optics A: Pure and Applied Optics 10, 025304 (2008); Tippie, A. E., Kumar, A., and Fienup, J. R., "High-resolution synthetic-aperture digital holography with digital phase and pupil correction," Opt. Express 19, pp. 12027-12038 (2011); Gutzler, T., Hillman, T. R., Alexandrov, S. A., and Sampson, D. D., "Coherent aperture-synthesis, wide-field, high-resolution holographic microscopy of biological tissue," Opt. Lett. 35, pp. 1136-1138 (2010); and Alexandrov, S. A., Hillman, T. R., Gutzler, T., and Sampson, D. D., "Synthetic aperture Fourier holographic optical microscopy," Phil. Trans. R. Soc. Lond. A 339, pp. 521-553 (1992), all of which are hereby incorporated by reference for the discussion of attempts to increase spatial bandwidth. Most of the above-described interferometric synthetic aperture techniques include setups that record both intensity and phase information using interferometric holography such as off-line holography and phase-shifting holography. Interferometric holography has its limitations. For example, interferometric holography recordings typically use highly coherent light sources. As such, the constructed images typically suffer from coherent noise sources such as speckle noise, fixed pattern noise (induced by diffraction from dust particles and other optical imperfections in the beam path), and multiple interferences between different optical interfaces. Thus the image quality is typically worse than from a conventional microscope. On the other hand, using off-axis holography sacrifices spatial-bandwidth product (i.e., reduces total pixel number) of the image sensor. A discussion of certain off-axis holography methods can be found in Schnars, U. and Jüptner, W. P. O., "Digital recording and numerical reconstruction of holograms," Measurement Science and Technology, 13, R85 (2002), which is hereby incorporated by reference for this discussion. In addition, interferometric imaging techniques may subject to uncontrollable phase fluctuations between different measurements. Hence, accurate a priori knowledge of the sample location may be needed to set a reference point in the image recovery process. Another limitation is that many of these interferometric imaging systems require mechanical scanning to rotate the sample and thus precise optical alignments, mechanical control at a sub-micron level, and associated maintenances are required by these systems. In terms of spatial-bandwidth product, these interferometric imaging systems may present little to no advantage as compared with a conventional microscope.

Previous lensless microscopy such as digital in-line holography and contact-imaging microscopy also present drawbacks. For example, conventional digital in-line holography does not work well with contiguous samples and contact-imaging microscopy requires a sample to be in close proximity to the sensor. A discussion of certain digital in-line holography devices can be found in Denis, L., Lorenz, D., Thiebaut, E., Fournier, C. and Trede, D., "Inline hologram reconstruction with sparsity constraints," *Opt. Lett.* 34, pp. 3475-3477 (2009); Xu, W., Jericho, M., Meinertzhagen, I., and Kreuzer, H., "Digital in-line holography for biological applications," *Proc. Natl Acad. Sci. USA* 98, pp. 11301-11305 (2001); and Greenbaum, A. et al., "Increased space-bandwidth product in pixel super-resolved lensfree on-chip microscopy," *Sci. Rep.* 3, page 1717 (2013), which are hereby incorporated by reference for this discussion. A discussion of certain contact-imaging microscopy can be found in Zheng, G., Lee, S. A., Antebi, Y., Elowitz, M. B. and Yang, C., "The ePetri dish, an on-chip cell imaging platform based on subpixel perspective sweeping microscopy (SPSM)," *Proc. Natl Acad. Sci. USA* 108, pp. 16889-16894 (2011); and Zheng, G., Lee, S. A., Yang, S. & Yang, C., "Sub-pixel resolving optofluidic microscope for on-chip cell imaging," *Lab Chip* 10, pages 3125-3129 (2010), which are hereby incorporated by reference for this discussion.

A high spatial-bandwidth product is very desirable in microscopy for biomedical applications such as digital pathology, haematology, phytotomy, immunohistochemistry, and neuroanatomy. For example, there is a strong need in biomedicine and neuroscience to digitally image large numbers of histology slides for evaluation. This need has prompted the development of sophisticated mechanical scanning and lensless microscopy systems. These systems increase spatial-bandwidth product using complex mechanisms with high precision to control actuation, optical alignment, and motion tracking. These complex mechanisms tend to be expensive to fabricate and difficult to use and maintain.

BRIEF SUMMARY OF THE INVENTION

Aspects of this disclosure concern imaging techniques, and more specifically methods, devices, and systems for Fourier ptychographic imaging.

Certain aspects pertain to aperture-scanning Fourier ptychographic imaging devices comprising optical elements, an aperture scanner that can generate an aperture at a plurality of locations at an intermediate plane of the optical elements, and a detector that can acquire lower resolution intensity images for different aperture locations, and wherein a higher resolution complex image may be constructed by iteratively updating regions in Fourier space with the acquired lower resolution images.

In some aspects, an aperture-scanning Fourier ptychographic imaging device comprises a first optical element configured to receive light from a sample and a second optical element. The device further comprises an aperture scanner configured to generate an aperture at a plurality of aperture locations in an intermediate plane, the aperture configured to pass incident light at the aperture from the first optical element to the second optical element. The device further comprises a radiation detector configured to receive light from the second optical element and to acquire a plurality of intensity images associated with different aperture locations. The device further comprises a processor configured to construct a complex image of the sample by iteratively updating regions in Fourier space with the acquired intensity images.

In some aspects, an aperture-scanning Fourier ptychographic imaging method comprises illuminating a sample, receiving incident light at a first optical element from the sample, generating an aperture at a plurality of locations at an intermediate plane, passing incident light at the aperture from the first optical element to a second optical element. The method further comprises acquiring a plurality of intensity images using a detector receiving light from the second optical element and constructing a complex image of the sample by iteratively updating regions in Fourier space with the plurality of intensity images.

These and other features are described in more detail below with reference to the associated drawings.

DETAILED DESCRIPTION OF THE INVENTION

Figure 1:
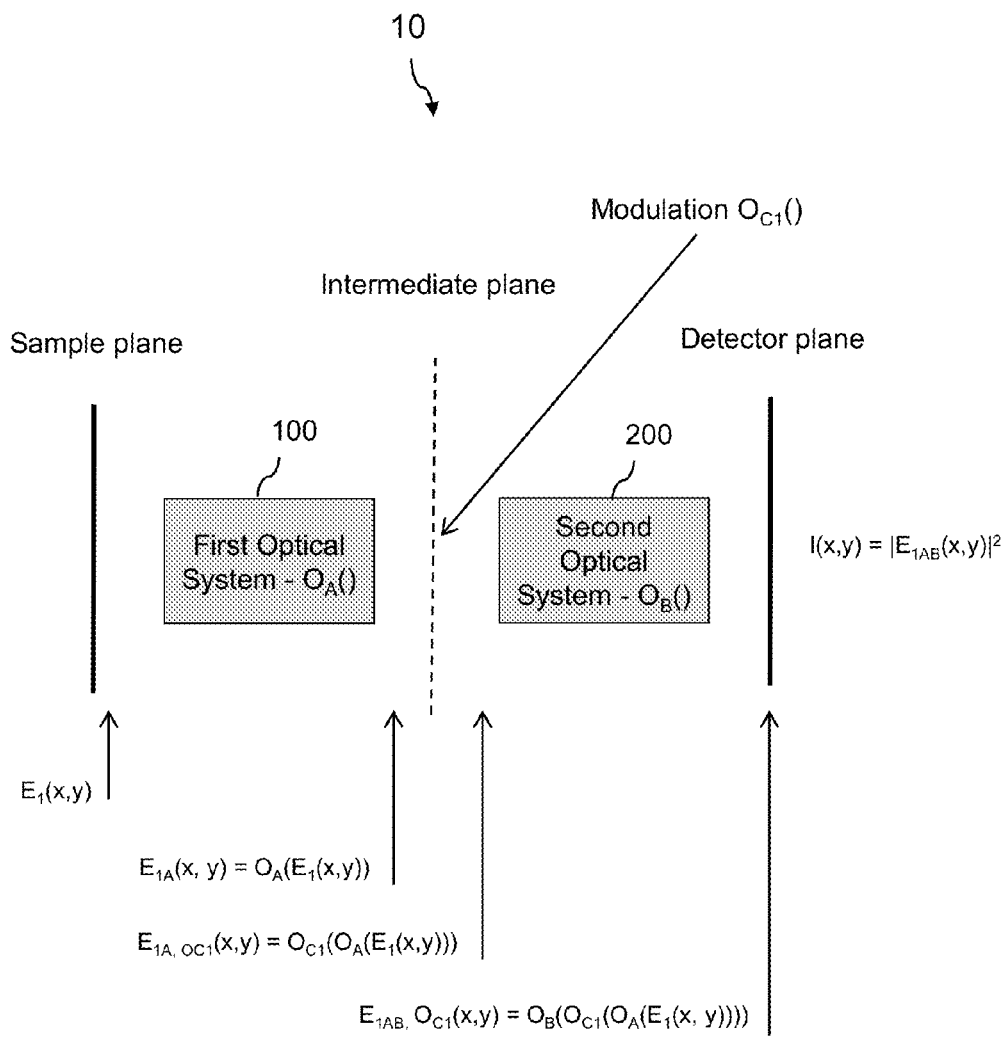
FIG. 1 illustrates a schematic drawing of components of a Fourier ptychographic imaging system with optical transfer function modulation at the intermediate plane.

Embodiments of the present invention will be described below with reference to the accompanying drawings. The features illustrated in the drawings may not be to scale.

I. Introduction

Fourier ptychography imaging implements a phase retrieval technique that uses angular diversity to recover complex sample images. The recovery process comprises alternating enforcement of known sample information in the spatial domain and a fixed constraint in the Fourier domain. The phase retrieval recovery may be implemented using any variant of an alternating projections algorithm, a convex reformulation of the problem, or any non-convex variant in-between. Instead of shifting a sample laterally (i.e. applying translational diversity), Fourier ptychography imaging uses a scanning spectrum constraint in the Fourier domain to expand the Fourier passband beyond that of a single captured image to recover an improved-resolution complex sample image.

Certain variable-angle illumination Fourier ptychography imaging systems use a variable illumination source (e.g., an LED array) to illuminate a sample being imaged from different illumination angles successively. An optical element such as a low numerical aperture objective lens filters light from the sample. A radiation detector receives the filtered light from the optical element and captures a intensity image of the sample at each illumination angle. Multiple resolution images may be iteratively stitched together in the Fourier domain to recover a higher resolution image of the image. Details of some variable-angle illumination Fourier ptychography systems, devices, and methods can be found in U.S. patent application Ser. No. 14/065,280, titled "Fourier Ptychographic Imaging Systems, Devices, and Methods" and filed on Oct. 28, 2013 and in U.S. patent application Ser. No. 14/065,305, titled "Fourier Ptychographic X-ray Imaging Systems, Devices, and Methods," which are hereby incorporated by reference for these details.

In some aspects, certain Fourier ptychography imaging systems described herein comprise an aperture scanner that can generate an aperture at a plurality of N aperture locations at an intermediate plane of the optical arrangement. For example, the aperture may be generated at a Fourier plane conjugate the sample plane. In some cases, a radiation detector receives light from the sample as modulated by the aperture at different locations, and acquires a plurality of M intensity images corresponding to the different aperture location. The M intensity images can be synthesized in the frequency domain to recover a complex, improved resolution image of the sample. In one aspect, optical aberrations and misalignments in the optical system(s) may be estimated and corrected through simulated annealing.

In certain aspects, an aperture-scanning Fourier ptychography imaging system comprises an aperture scanner that can generate an aperture at a plurality of N aperture locations at different times in an intermediate plane (e.g., Fourier plane) of an optical arrangement. In other aspects, an aperture-scanning Fourier ptychography imaging system comprises an aperture scanner that can generate a plurality of apertures that are shifted as a whole to a plurality of N locations at different times in an intermediate plane of the optical arrangement. Such a plurality of apertures may be in pattern form (e.g., checkered pattern) or in an random order.

As used herein, an aperture can refer to an area in a plane that allows incident light to pass to the next optical element in the optical arrangement. In some cases, an area surrounding the aperture at that plane may block/reflect or otherwise prevent incident light from passing to the next optical element. In certain aspects, the aperture may be an optically transparent or substantially optically transparent area. In these aspects, the surrounding area may reflect or absorb the incident light. For example, the aperture may be a light transmissive region (e.g., hole) in an opaque plate. In other aspects, the aperture may a reflective area (e.g., one or more micromirrors or one or more reflective pixels in a display) that reflects incident light to the next optical element. In these aspects, the surrounding area may either absorb incident light or reflect incident light away from the next optical element. In one example, the aperture may be comprised of one or more micromirrors oriented at an angle that reflects incident light to the next optical element. In this example, one or more micromirrors in the surrounding area may be oriented at a different angle that reflects light away from the next optical element. In some cases, an aperture location may correspond to a centroid of the area of the aperture.

In certain aspects, aperture-scanning Fourier ptychography imaging systems may comprise mechanically-based aperture scanners and/or display-based aperture scanners. Certain mechancially-based aperture scanners can mechanically shift an aperture to different aperture locations. In one case, a mechancially-based aperture scanner comprises an X-Y translational stage that can translate/rotate a structure (e.g., plate of opaque material having an aperture in the form of a light transmissive region such as a hole in the plate) having the aperture to shift the aperture to the plurality of aperture locations in the intermediate plane. Certain display-based aperture scanners can digitally generate an aperture at different locations, for example, by displaying an aperture and surrounding area on a display. Some examples of display-based aperture scanners include a spatial light modulator (SLM) that generates an aperture and surrounding area on an SLM display. The SLM display may be, for example, a liquid crystal on silicon (LCoS) display or a digital micromirror device (DMD).

Certain aperture-scanning Fourier ptychographic systems and methods described herein may provide one or more technical advantages. One advantage of certain systems is that they can be used for imaging of thick and/or non-transmissive samples. Another advantage of certains systems is that they can be adapted for luminescence (e.g., fluorescence, phosphorescence, chemluminescence, bioluminescence, etc.) imaging.

Certain aperture-scanning Fourier ptychographic systems described herein can be adapted for luminescence (e.g., fluorescence, phosphorescence, chemluminescence, bioluminescence, etc.) imaging. For example, certain systems may be adapted to collect emissions directed back toward the illumination source.

In trans-illumination imaging configurations, a light detector may acquire light data about light transmitted through the sample. For example, the illumination source may direct illumination toward the light detector where the sample is located between the light detector and the illumination source. In these trans-illumination imaging configurations, light reflected back toward the illumination source or emitted by the sample in the direction of the illumination source may not be received by the light detector.

In fluorescence imaging and other luminescence imaging applications, fluorophores in the sample are excited by excitation illumination of a certain wavelength(s) from the illumination source and emit light of a different wavelength(s) (emissions). These emissions tend to have a weak signal compared to the excitation light so that collection efficiency may be important.

In some aspects, certain aperture-scanning Fourier ptychographic systems may be configured so that the light detector can receive emissions from the sample and/or light reflected from the sample back toward the illumination source. These systems have optical arrangements that can accommodate an illumination source that directs excitation illumination to the sample and away from next element in the system. In this way, propagation of the excitation illumination through the system may be substantially avoided.

In some aspects, certain aperture-scanning Fourier ptychographic imaging systems can be used to image thick and/or non-transparent samples. In these systems, a single arbitrarily patterned coherent illumination beam may be used to illuminate the sample from any direction. For these systems, there is a one-to-one relationship between each of the intensity images and different passbands of the 2D sample spectrum for both thick and non-transparent samples. Thus, the recovery process can accurately impose the panning spectrum constraint to recover a higher-resolution (i.e. improved resolution) complex image of thick and/or non-transparent samples.

II. Optical Transfer Function Modulation in Ptychographic Fourier Imaging

In imaging systems, a sample may be illuminated by a light field and the optical field $E_1(x, y)$ emerging from the sample surface may be generally described as: $E_1(x, y) = A_1(x,y)e^{i\varphi 1(x,y)}$. Certain ptychographic Fourier imaging systems can be used to characterize $E_1(x,y)$ and determine an aberration-free set of amplitude and phase data about the sample. In certain aspects, a ptychographic Fourier imaging system can be used to determine a phase and amplitude distribution of the optical field $E_1(x, y)$ to simultaneously correct for optical aberrations and/or misalignments in the system as the sample is imaged.

An optical field $E_1(x, y)$ may be transmitted through an optical system to generate an optical field $E_2(x, y) = O(E_1(x, y))$ where $O(\ )$ represents the optical transfer function performed on the light field by the optical system. $O(\ )$ can be represented by any number of different operations. For example, $O(\ )$ can be represented as a Fourier transform (e.g., if the system is a simple lens with a sample at its focus plane and projection screen at infinity); it can be a unitary transformation (e.g., if the system is a perfect 4f system); or it can be a complex function. Optical aberrations are expressible within the optical transfer function. For example, a physical optical system may not perform a perfect Fourier transform, but its aberrations can be mathematically described as the ways it distorts the transform function. $O(\ )$ function may be fully characterizable by any number of characterization means. Typically, the $E_2(x,y)$ may be measured or put through additional optical systems prior to subsequent measurements. Suppose $E_2(x,y)$ is measured by some means such as, for example, a light detector (e.g. digital camera). The intensity values measured may be expressed as: $|E_2(x,y)|^2$. With only this amplitude measurement, it may not be possible to apply an inverse function to get $E_1(x,y)$. On the other hand, if both amplitude and phase knowledge of $E_2(x,y)$ are known and the function $O(\ )$ is known, then $E_1(x,y)$ can be obtained by taking the inverse $O(\ )$ function of $E_2(x,y)$. That is, $E_1(x,y) = O^{-1}(E_2(x,y))$.

In certain aspects, Fourier ptychographic imaging systems with modulation at the intermediate plane can be used determine both amplitude and phase data of an optical field $E_1(x, y)$ at the sample plane. In some cases, modulation may be implemented by an aperture scanner.

FIG. 1 illustrates a schematic drawing of certain components of a Fourier ptychographic imaging system 10 with optical transfer function modulation at an intermediate plane, according to embodiments. In one example, the optical function modulation may be implemented with an aperture scanner generating an aperture at N different locations at the intermediate plane such as, for example, a Fourier plane of the sample plane of the optical system. In one case, the aperture scanning Fourier ptychographic imaging system 10 may be able to determine amplitude and phase data of the optical field $E_1(x,y)$ at a spatial resolution near or at the optical limit dictated by the numerical aperture (NA) of the system 10.

In FIG. 1, the aperture-scanning Fourier ptychographic imaging system 10 comprises a first optical system 100 with an optical transfer function of $O_A(\ )$ and a second optical system 200 with an optical transfer function of $O_B(\ )$. According to the schematically represented light fields in FIG. 1, the optical field $E_1(x, y)$ from the sample is received by the first optical system 100. The resulting light field function is given by $E_{1A}(x,y) = O_A(E_1(x,y))$. In some cases, rough estimates of the optical transfer functions $O_A(\ )$ and $O_B(\ )$ of the first and second optical systems 100, 200 respectively may be used as an initial starting point in a joint optimization procedure to determine a more accurate complex optical transfer function estimate, in conjunction with the running of the Fourier ptychography recovery algorithm, such as described in Xiaoze Ou, Guoan Zheng and Changhuei Yang, Embedded pupil function recovery for Fourier ptychographic microscopy," Optics Express 22 (5), pp. 4960-4972 (2014), which is hereby incorporated by reference for this description.

If this system did not have modulation at the intermediate pane, the light field from the first optical system 100 would propagate to the second optical system 200, which would result in a final light field function of $E_{1AB}(x, y) = O_B(O_A(E_1(x, y)))$. The intensity distribution, $I(x, y) = |E_{1AB}(x, y)|^2$ of the final light field can be measured spatially at the detector plane. In this case, the measured intensity distribution $I(x, y)$ may not provide enough information to determine $E_1(x, y)$ or $E_{1A}(x, y)$ since the phase information is not measured by the light detector (only the amplitude).

In FIG. 1, the aperture function or other known modulating function with an optical transfer function of $O_{C1}(\ )$ is applied at the intermediate plane. In this case, the light field modulated at the intermediate plane propagates to second optical system 200, which results in a final light field function of $E_{1A,\ OC1}(x,y) = O_{C1}(O_A(E_1(x,y)))$.

The aperture-scanning Fourier ptychographic imaging system 10 can use a Fourier ptychographic method to determine both amplitude and phase data of $E_1(x, y)$. First, a guess of $E_1(x, y)$ is made designated as $E_{1guess}(x, y)$. Next, the aperture function or other known modulating function is applied at the intermediate plane of $E_{1A}(x, y)$. This aperture function may be an optical transfer function designated as $O_{C1}(\ )$ and the new $E_{1A,\ OC1}(x,y) = O_{C1}(O_A(E_1(x,y)))$. The new $E_{1AB},O_{C1}(x,y) = O_B(O_{C1}(O_A(E_1(x,y))))$. The $|E_{1AB},O_{C1}(x,y)|^2$ is determined by acquiring the intensity distribution at the detector plane. Next, $E_{1A,\ OC1,\ guess}(x,y) = O_B(O_{C1}(O_A(E_{1guess}(x,y))))$ and $|E_{1AB},O_{C1,guess}(x,y)|^2$ are computationally determined and $|E_{1AB},O_{C1}(x,y)|^2$ is compared to $|E_{1AB},O_{C1,guess}(x, y)|^2$. If the comparison shows a difference (i.e., they are not equal to each other), a new $E_{1guess}(x, y)$ is generated by modifying the current $E_{1guess}(x, y)$ based on known restrictions on $E_{1A},O_{C1}(x, y)$ and $|E_{1AB},O_{C1}(x, y)|^2$. One strategy for modifying the guess is provided below. This process of modification of $E_{1guess}(x, y)$ is iterated by applying the aperture or other known function at a different location at the plane of $E_{1A}(x,y)$ (e.g., at $O_{C1}(\ )$, $O_{C2}(\ )$, $O_{C3}(\ )$, . . . ) until we have reached convergence where $|E_{1AB},O_{Cn}(x, y)|^2$ is equal (or substantively equal based on error function measures) to $|E_{1AB},O_{Cn,guess}(x, y)|^2$ for all $O_{Cn}(\ )$ functions where n=1, 2, 3 . . . .

III. Aperture-Scanning Ptychographic Fourier Imaging

Certain aspects described herein pertain to aperture-scanning Fourier ptychographic imaging systems, devices and methods. The Fourier ptychographic imaging systems comprise an aperture scanner. In certain aspects, the aperture scanner can generate an aperture at a plurality of N aperture locations at different times in an intermediate plane of an optical arrangement. In other aspects, the aperture scanner can generate a plurality of apertures that are shifted as a whole to a plurality of N locations at different times in an intermediate plane of the optical arrangement. The intermediate plane may be, for example, a Fourier plane conjugate the sample plane. The Fourier ptychographic imaging systems further comprise a light detector at a detector plane that is configured to acquire a plurality of M intensity images of the sample.

An aperture scanner can refer to one or more devices configured to generate the aperture (or plurality of apertures) at a plurality of N locations at an intermediate plane. In certain cases, each intensity image of the plurality of M intensity images acquired by the light detector corresponds to a different aperture location of the plurality of N aperture locations. The number of aperture locations N and/or number of intensity images M may be in the range of 1 to several thousand. In one case, N and/or M may be a value in a range from 1 to 1000. In another case, N and/or M may be a value in a range from 1 to 2000. In another case, N and/or M may be a value in a range from 1 to 3000. In some examples, N=M.

Although the apertures described herein with reference to certain illustrations are rectangular in shape having dimensions of width l and height h, other shapes such as a circular shape with radius r, triangular, etc., may be used. In addition, the aperture at different locations of the plurality of N aperture locations is described in examples as being of constant shape and size. It would be understood however that the aperture can be of varying sizes and shapes at different aperture locations. In one case, the area of the aperture has a size of 0.5 mm×0.5 mm. In another case, the area of the aperture has a size of 5 mm×5 mm.

The plurality of N aperture locations may be described in the form of a one-dimensional array, a two-dimensional matrix, a hexagonal array, etc. In some cases, the plurality of aperture locations may be a two-dimensional matrix in the form of a rectilinear grid (e.g., square grid), a curvilinear grid, etc. If the plurality of N aperture locations is in a rectilinear grid arrangement having dimensions m×n, then the aperture locations may be designated as $(X_i, Y_j)$, i=1 to m, j=1 to n and the number of aperture locations, N=m×n. If such a rectilinear grid has square dimensions of n×n, then the aperture locations may be designated as $(X_i, Y_j)$, i=1 to n, j=1 to n and $N=n^2$.

The N aperture locations can be generated in any order (e.g., sequential, random, row by row, column by column, etc.) over time during the image acquisition process. For example, a sequential column by column order through a rectilinear grid may be: $(X_1,Y_1), (X_1,Y_2), (X_1,Y_3), \ldots (X_1,Y_n), (X_2,Y_1), (X_1,Y_2), (X_1,Y_3), \ldots (X_2,Y_n), \ldots (X_m,Y_n)$ at sample times $t_i$=1 to M, where M=m×n. Alternatively, a random order may be used.

In certain aspects, the plurality of N aperture locations includes an overlapping area between two or more of its neighboring apertures (i.e. apertures at adjacent aperture locations). In one example, the overlapping area may be about 70% of the aperture area. In another example, the overlapping area may be about 75% of the aperture area. In another example, the overlapping area may be between about 2 and 90% of the aperture area. In some cases, particular values of m and n may be used so that neighboring apertures overlap by a predefined amount (e.g., 70%, 75%, etc.).

In some aspects, mechancially-based aperture scanners can mechanically shift an aperture to different aperture locations. For example, a mechanically-based aperture scanner may comprise an X-Y stage configured to physically translate and/or rotate a structure having an aperture (e.g., plate of opaque material having an aperture in the form of a light transmissive region such as a hole in the plate) to generate the aperture at the different aperture locations. In one example, a plate with an aperture may be affixed to the X-Y stage and the X-Y stage may then translate and/or rotate the plate in the intermediate plane to locate the aperture at the appropriate aperture locations at the corresponding acquisition times. In one case, the plate may have a surface with the aperture located orthogonal to the surface. The X-Y stage may translate/rotate the plate so that the surface remains in the intermediate plane.

In some aspects, display-based aperture scanners can digitally display an aperture at different aperture locations. An example of a display-based aperture scanner is a spatial light modulator or SLM. A "spatial light modulator" or "SLM" can refer to a device(s) that can generate an aperture on its display. In some cases, an SLM uses an electrical and/or optical signal from an SLM light source to modulate phase, φ, and/or amplitude of light. In some cases, the SLM light source may be a collimated light source such as a laser (e.g., Excelsior® 532 SM). In other cases, the SLM light source may not be collimated light. For example, the light may be spatially filtered light from a light emitting diode (spatial coherence length of approximately 1 mm, spectral bandwidth of 20 nm), or light from a laser source (e.g., 532 nm quasi-monochromatic laser light, spatial coherence length of multiple meters). The SLM light source may be a component of the aperture-scanning Fourier ptychographic imaging system or may be a separate component. Certain SLMs may be commercially available. In certain aspects, an SLM comprises an SLM display having a plurality of SLM display elements. Each SLM display element can be set to function as an aperture (aperture setting) or to function as the area surrounding the aperture (field setting). In some configurations, an SLM display element in an aperture setting is transparent or nearly transparent to pass incident light and a display element in a field setting may block/reflect or nearly bock/reflect incident light. In other configurations, certain SLM display elements may be reflective. In these cases, a display element in the aperture setting is oriented at a (first) angle to reflect incident light to the next optical element in the optical arrangement and a display element in a field setting is oriented at a different (second) angle that reflects incident light away from the next optical element. In these configurations, the SLM display can generate an aperture at one or more SLM display elements by setting these display elements in an aperture setting and/or setting the surrounding display elements in a field setting. At different acquisition times, $t_i$, different sets of one or more display elements are at appropriate settings to generate the aperture at the corresponding aperture location. In some cases, the SLM display may have a refresh rate in the range of 30 per second to 100 per second.

Figure 4:
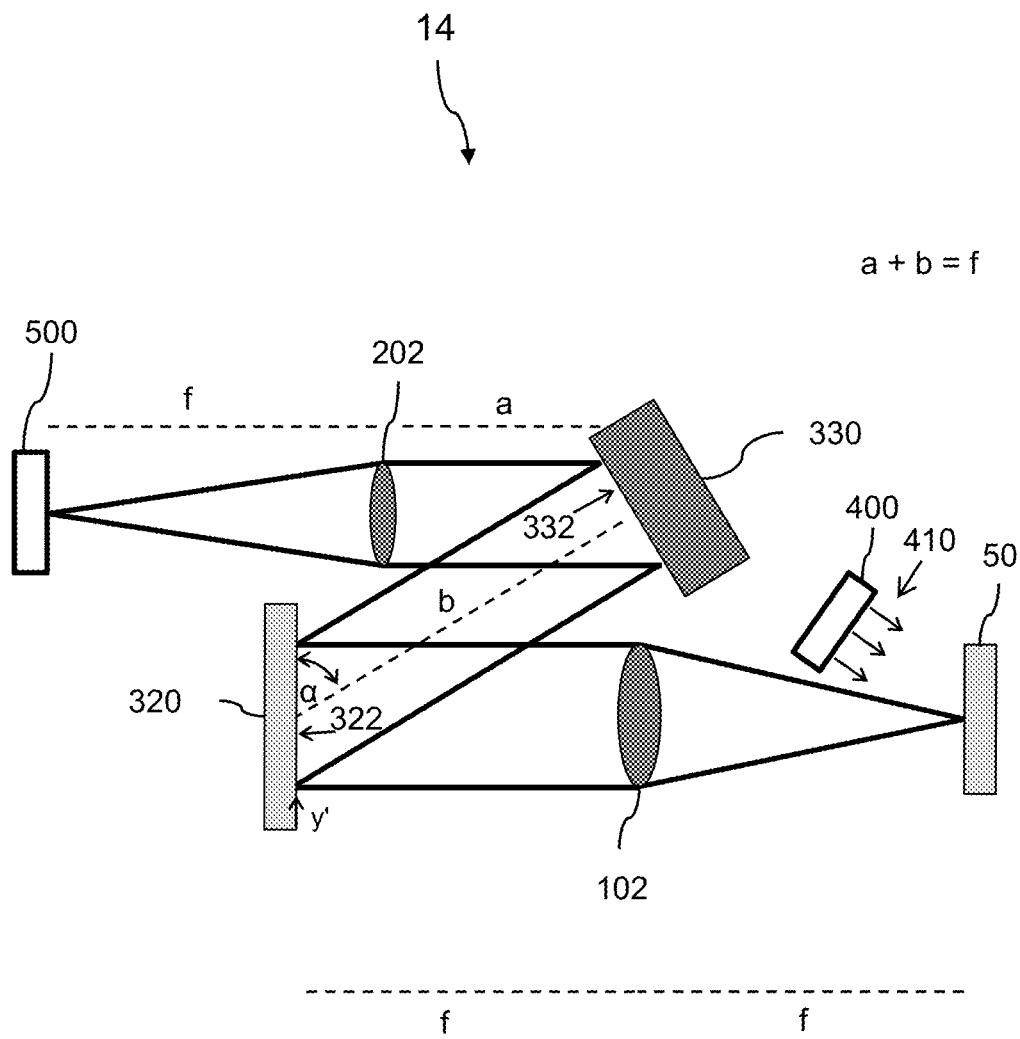
FIG. 4 is a schematic drawing of components of an aperture-scanning Fourier ptychographic imaging system comprising a DMD array.
Figure 5:
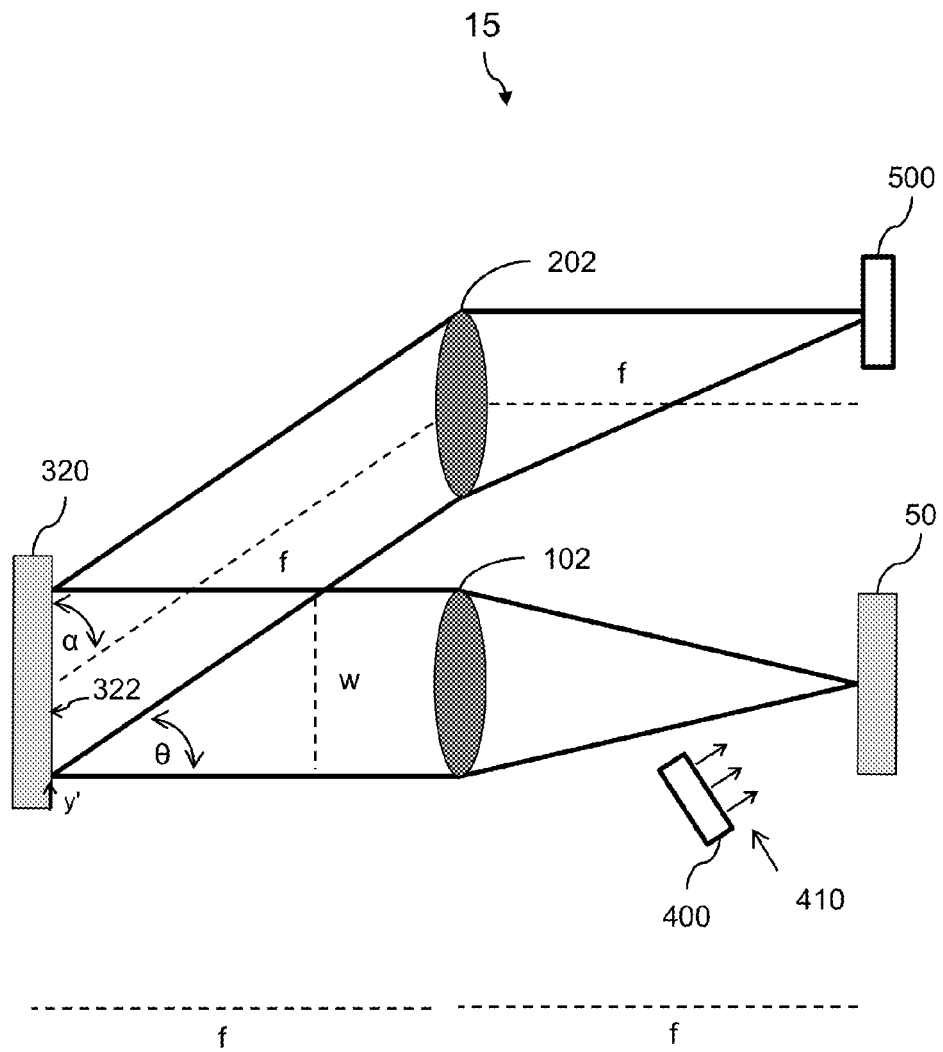
FIG. 5 is a schematic drawing of components of an aperture-scanning Fourier ptychographic imaging system comprising a DMD array.

In aperture-scanning Fourier ptychographic imaging systems comprising an aperture scanner in the form of an SLM, different types of SLM displays may be used such as, for example, a reflective liquid-crystal on silicon (LCoS) display, a digital micromirror device (DMD), etc. A reflective liquid-crystal on silicon (LCoS) display is a reflective display having a plurality of reflective display elements. An example of a commercially available LCoS display is the reflective HOLOEYE® SLM, Pluto, phase only LCoS, 8 μm pixel size, 1080×1920 pixels display. A DMD can refer to an optical semiconductor chip having on its surface multiple microscopic micromirrors. In certain aspects, each micromirror can be individually rotated to an angle, a. In this way, each micromirror can be transitioned to either an aperture setting at angle, a, or to a field setting at no rotation, or visa versa Although these micromirrors are usually arranged in a rectangular array (dimensions o×p), other arrangements may be used. In certain aspects, each micromirror of the DMD may correspond to one or more light detector pixels. In one case, one or more of the micromirrors in the aperture setting may be oriented so that an optical axis orthogonal to the surface of the micromirror is oriented at an angle, a, from the Fourier plane. An example of this case is shown in FIGS. 4 and 5.

In aperture-scanning Fourier ptychographic imaging systems comprising an aperture scanner in the form of an SLM, the SLM display may be located so that its display plane at the intermediate plane (e.g., Fourier plane). In some cases, the SLM display may be in the form of a two-dimensional matrix of display elements (e.g. pixels) at the display plane. The two-dimensional matrix has dimensions of $Pix_1 \times Pix_2$, where $Pix_1$ is the number of pixels in a first direction and $Pix_2$ is the number of pixels in a second direction orthogonal to the first direction. In one example, the SLM display is a 1920-by-1080 pixel display where $Pix_1$ is 1920 and $Pix_2$ is 1080. In certain aspects, the display elements of the SLM are programmed to have particular settings at different acquisition times according to illumination instructions.

A sample being imaged by aperture-scanning Fourier ptychographic imaging systems may be comprised of one or more objects or one or more portions of an object. Each object may be a biological entity or an inorganic entity. Examples of biological entities include whole cells, cell components, microorganisms such as bacteria or viruses, cell components such as proteins, thin tissue sections, etc. In some cases, the sample may be provided in a medium such as a liquid.

In luminescence imaging examples, a reagent (e.g., fluorescence/phosphorescence dye) may be mixed with the sample to mark or tag portions under investigation with fluorophore. A fluorophore can refer to a component of a molecule that causes the molecule to fluoresce or phosphoresce. A fluorophore can absorb energy from excitation light of a specific wavelength(s) and re-emit the energy at a different wavelength(s). In luminescence imaging examples, the illumination source illuminates the sample with excitation light of predetermined wavelength(s) (e.g., blue light) to activate the fluorophore in the sample. In response, the fluorophore release emissions of a different wavelength(s) (e.g., red light).

In certain aspects, an illumination source(s) provides illumination to the sample being imaged by an aperture-scanning Fourier ptychographic imaging system. The illumination source may be a component of or separate from the aperture-scanning Fourier ptychographic imaging system. Although the illumination source is described in some cases as being located to direct illumination toward the first optical element in the optical arrangement, the illumination source may be located in other locations to direct illumination away from the first optical element. For example, in a luminescence imaging example, the illumination source(s) may provide excitation light that is directed away from the first optical system in the optical arrangement. In many cases, excitation illumination has a stronger signal than emissions from the sample. By directing the excitation illumination away from the first optical system, this configuration will aid in collecting a weaker emissions signal by the light detector. Although a single illumination source is described in many cases, it would be understood that multiple illumination sources may be used.

In certain cases, the aperture-scanning Fourier ptychographic imaging techniques pertain to a sample illuminated by a single arbitrarily patterned coherent illumination beam from any direction. In many cases, the angle of illumination does not vary during the image acquisition process. In some cases, the illumination may be monochromatic. In another case, the illumination source may provide illumination of different wavelengths (e.g., wavelengths associated with RGB) at different acquisition times as discussed below. Although the illumination source(s) may be coherent source(s), incoherent source(s) may also be used and computational corrections may be applied. Some examples of a source of visible light include an LCD pixel and a pixel of an LED display. In cases that use other forms of radiation, other sources of radiation may be used. For example, in embodiments that use X-ray radiation, the radiation source may comprise an X-ray tube and a metal target. As another example, in cases that use microwave radiation, the radiation source may comprise a vacuum tube. As another example, in cases that use acoustic radiation, the radiation source may be an acoustic actuator. As another example, in cases that use Terahertz radiation, the radiation source may be a Gunn diode. One skilled in the art would contemplate other sources of radiation.

In color imaging implementations, the illumination source may provide RGB illumination of three wavelengths $\lambda 1$, $\lambda 2$, and $\lambda 3$ corresponding to red, green, blue colors, respectively. In one case that uses Terahertz radiation, the frequencies of the radiation provided by the illumination source may be in the range of 0.3 to 3 THz. In one case that uses microwave radiation, the frequencies of the radiation provided by the variable illuminator may be in the range of 100 MHz to 300 GHz. In one case that uses X-ray radiation, the wavelengths of the radiation provided by the variable illuminator may be in the range of 0.01 nm to 10 nm. In one case that uses acoustic radiation, the frequencies of the radiation provided by the variable illuminator may be in the range of 10 Hz to 100 MHz.

In certain aspects, a "radiation detector" or "light detector" or "detector" is configured to acquire an intensity image of the sample by measuring/recording an intensity distribution of incident radiation at a detector plane at a particular sample (acquisition) time. During an image acquisition process, for example, the radiation detector may acquire a plurality of M intensity images at M sample times, $t_{i=1 \text{ to } M}$. If visible light radiation is being measured, the radiation detector may be in the form of a charge coupled device (CCD), a CMOS imaging sensor, an avalanche photo-diode (APD) array, a photo-diode (PD) array, a photomultiplier tube (PMT) array, or like device. If using THz radiation is detected, the radiation detector may be, for example, an imaging bolometer. If using microwave radiation is used, the radiation detector may be, for example, an antenna. If us X-ray radiation is used, the radiation detector may be, for example, an x-ray sensitive CCD. If using acoustic radiation is used, the radiation detector may be, for example, a piezoelectric transducer array. These examples of radiation detectors and others are commercially available. In some cases, the radiation detector may be a color detector e.g. an RGB detector. In other cases, the radiation detector need not be a color detector. In certain cases, the radiation detector may be a monochromatic detector.

A "sample" or "acquisition" time can refer to a time that the light detector captures an intensity image of the sample. During certain image acquisition processes described here, the radiation detector captures a plurality of M intensity images (e.g., M=1, 2, 5, 10, 20, 30, 50, 100, 1000, 10000, etc.). At each sample time, $t_i$, that an intensity image is captured, the aperture is at a different scanning location of the plurality of N aperture locations. In certain cases, the sampling rates may range from 0.1 to 1000 frames per second.

In certain aspects, the radiation detector may have discrete radiation detecting elements (e.g., pixels). The radiation detecting elements may be of any suitable size (e.g., 1-10 microns) and any suitable shape (e.g., circular, rectangular, square, etc.). For example, a CMOS or CCD element may be 1-10 microns and an APD or PMT light detecting element may be as large as 1-4 mm. In one example, the radiation detecting element is a square pixel having a size of 5.5 um.

The radiation detector generates image data comprising the plurality of M intensity images. The radiation detector may also generate other image data such as the sample times and other related data.

Fourier space can refer to a mathematical space spanned by wavevectors $k_x$ and $k_y$, being the coordinate space in which the two-dimensional Fourier transforms of the spatial images created by the aperture-scanning Fourier ptychographic imaging system reside. Fourier space may also refer to the mathematical space spanned by wavevectors $k_x$ and $k_y$, in which the two-dimensional Fourier transforms of the spatial images collected by the radiation sensor reside.

Each of the plurality of M intensity images captured by the radiation detector is associated with a region in Fourier space. In Fourier space, neighboring regions may share an overlapping area over which they sample the same Fourier domain data. This overlapping area in Fourier space corresponds to the overlapping area of neighboring apertures in the intermediate plane. In certain aspects, the plurality of N aperture locations is designed so that the overlapping area of neighboring aperture locations will generate a certain amount of overlapping area in the Fourier domain data. In one case, the plurality of aperture locations are designed to generate an overlapping area in the Fourier domain data in the range of about 2% to about 99.5% of the area of one of the regions. In another embodiment, the overlapping area between neighboring regions may have an area that is in the range of 65% to 75% the area of one of the regions. In another embodiment, the overlapping area between neighboring regions may have an area that is about 65% of the area of one of the regions.

Figure 2A:
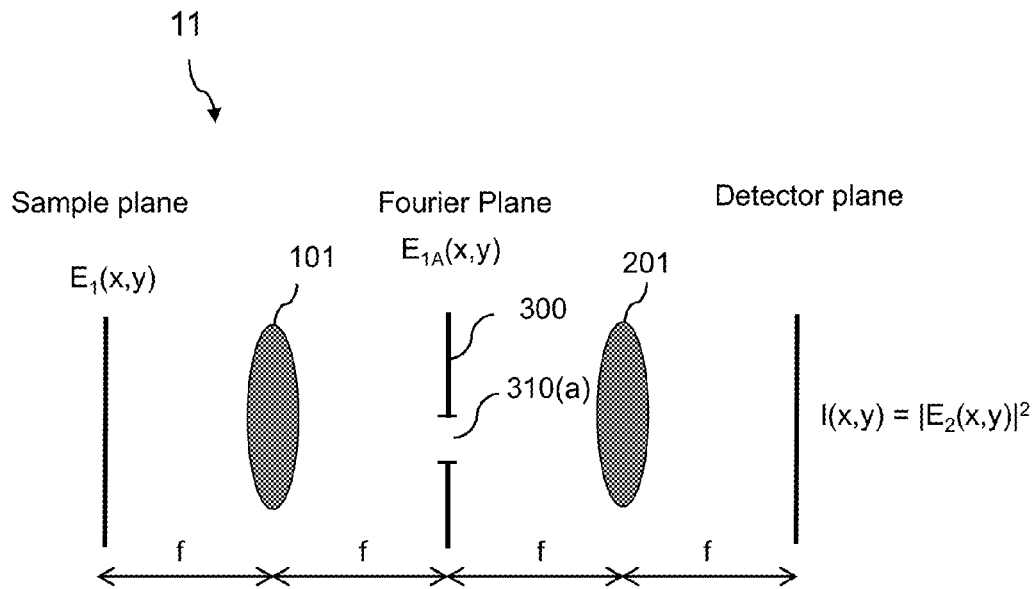
FIGS. 2A and 2B are schematic drawings of components of an aperture-scanning Fourier ptychographic imaging system.
Figure 2B:
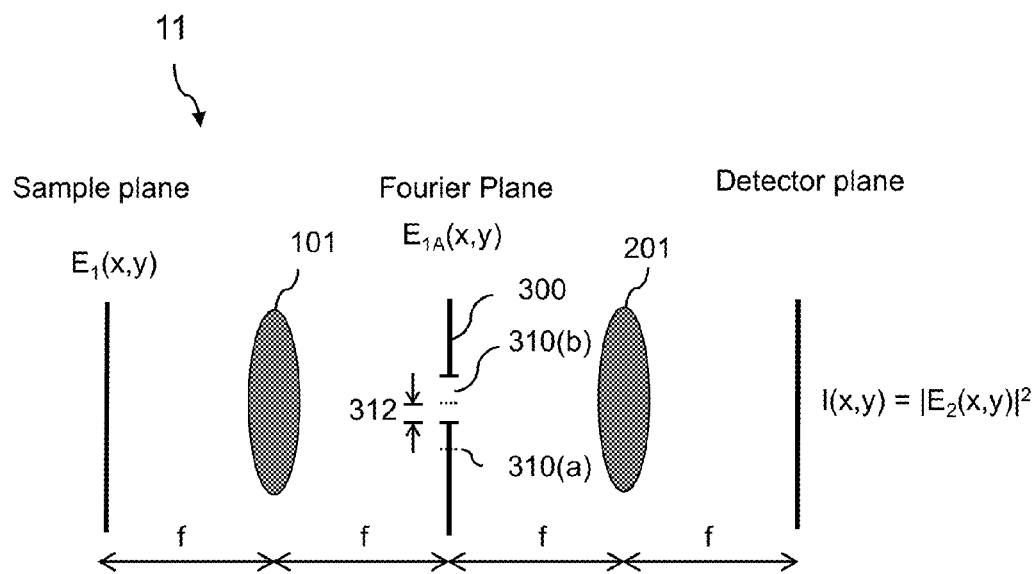

FIGS. 2A and 2B are schematic drawings of components of an aperture-scanning Fourier ptychographic imaging system 11, according to embodiments. In this illustration, the optical elements are in a 4f optical arrangement and aperture scanning is at a Fourier plane of the sample. The aperture-scanning Fourier ptychographic imaging system 11 comprises a first optical system (e.g., lens) 101 having a first focal length $f_1$ (where $f_1$=f) a second optical system (e.g., lens) 201 having a second focal length $f_2$ (where $f_1$=f), and an aperture scanner 300. The aperture-scanning Fourier ptychographic imaging system 11 also includes a sample plane, a detector plane, and a Fourier plane of the sample (not shown). During image acquisition, a sample being imaged is located at the sample plane. Although not shown, the aperture-scanning Fourier ptychographic imaging system 11 further comprises a detector at the detector plane. Optionally, the aperture-scanning Fourier ptychographic imaging system 11 may further comprise an illumination source for illuminating the sample. Also optionally, the aperture-scanning Fourier ptychographic imaging system 11 may further comprise one or more components of a computing device comprising a processor, a display in communication with the processor, and a computer readable medium.

According to the 4f optical arrangement shown in FIGS. 2A and 2B, the first optical system 101 is located at a distance from the second optical system 201 equal to their combined focal lengths 2f. The sample plane is located at an optical path distance of the first focal length from the first optical system 101 and the detector plane is located an optical path distance of a second focal length from the second optical system 201. The Fourier plane of the sample is located at distance of a first focal length from the first optical system 101 and located at an optical path distance of the second focal length from the second optical system 201.

The illustrated aperture-scanning Fourier ptychographic imaging system 11 also includes an aperture 310. The aperture-scanning Fourier ptychographic imaging system 11 may further comprise an aperture scanner 300 configured to provide the aperture 310 at a plurality of aperture locations in the Fourier plane.

In this illustrated example, the aperture is shown at two neighboring aperture locations at different sampling times. FIG. 2A shows the aperture 310(a) at a first aperture location. FIG. 2B shows aperture 310(b) at a second aperture location. FIG. 2B also shows aperture 310(a) in a dotted line to illustrate the overlapping region 312 between the two adjacent aperture locations.

During certain image acquisition processes, the aperture scanner of an aperture-scanning Fourier ptychographic imaging system generates an aperture at a plurality of N aperture locations $(X_i, Y_j)$, i=1 to n, j=1 to m, M=n×m. At neighboring aperture locations in the plurality of aperture locations there is an overlapping region (e.g., 312) between neighboring aperture locations. At the detector plane, the light detector acquires an intensity image while the aperture is at a corresponding aperture scanning position. During the image acquisition process, the light detector acquires a plurality of M intensity images corresponding to different aperture locations. The M intensity images (i.e. $I_{i,j}$, i=1 to o, j=1 to p and M=o×p) are acquired at the detector plane at acquisition times, $t_{i,j}$, i=1 to o, j=1 to p. The number of intensity images, M, acquired by the light detector can be in the range of 1 to a few thousand intensity images. During certain image recovery processes, an aperture-scanning Fourier ptychographic imaging system recovers a higher resolution, complex field $E_1(x, y)$ at the sample plane from the plurality of M intensity images. In certain aspects, the complex field at the sample plane can then be propagated to various planes (e.g., planes parallel to the sample plane). These propagated images can be used to form a 3D image of an extended sample.

Details of certain Fourier ptychographic acquisition and recovery processes can be found in Section IV below. An example of an Fourier ptychographic recovery process can also be found in Guoan Zheng, Roarke Horstmeyer, and Changhuei Yang, "Wide-field, high-resolution Fourier ptychographic microscopy," Nature Photonics 6, pp. 739-745 (2013), which is hereby incorporated by reference in its entirety. Certain details of an aperture-scanning Fourier ptychographic imaging system can be found in Dong, Siyuan et al., "Aperture-scanning Fourier ptychography for 3D refocusing and super-resolution macroscopic imaging," pp. 13586-13599 (Jun. 2, 2014), which is hereby incorporated by reference in its entirety.

Figure 3A:
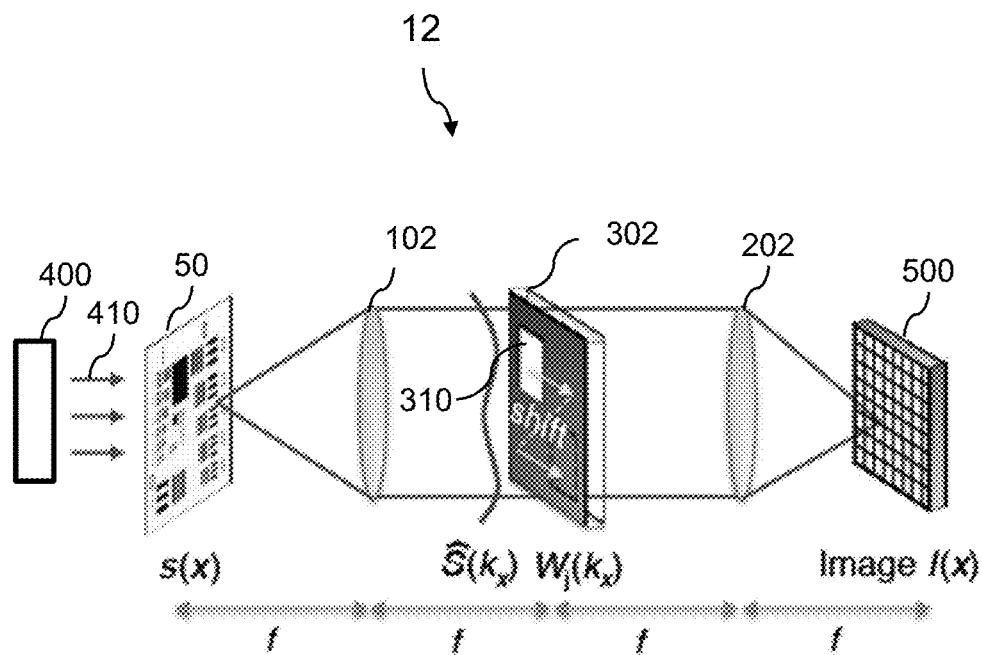
FIG. 3A is a schematic drawing of components of an aperture-scanning Fourier ptychographic imaging system.
Figure 6:
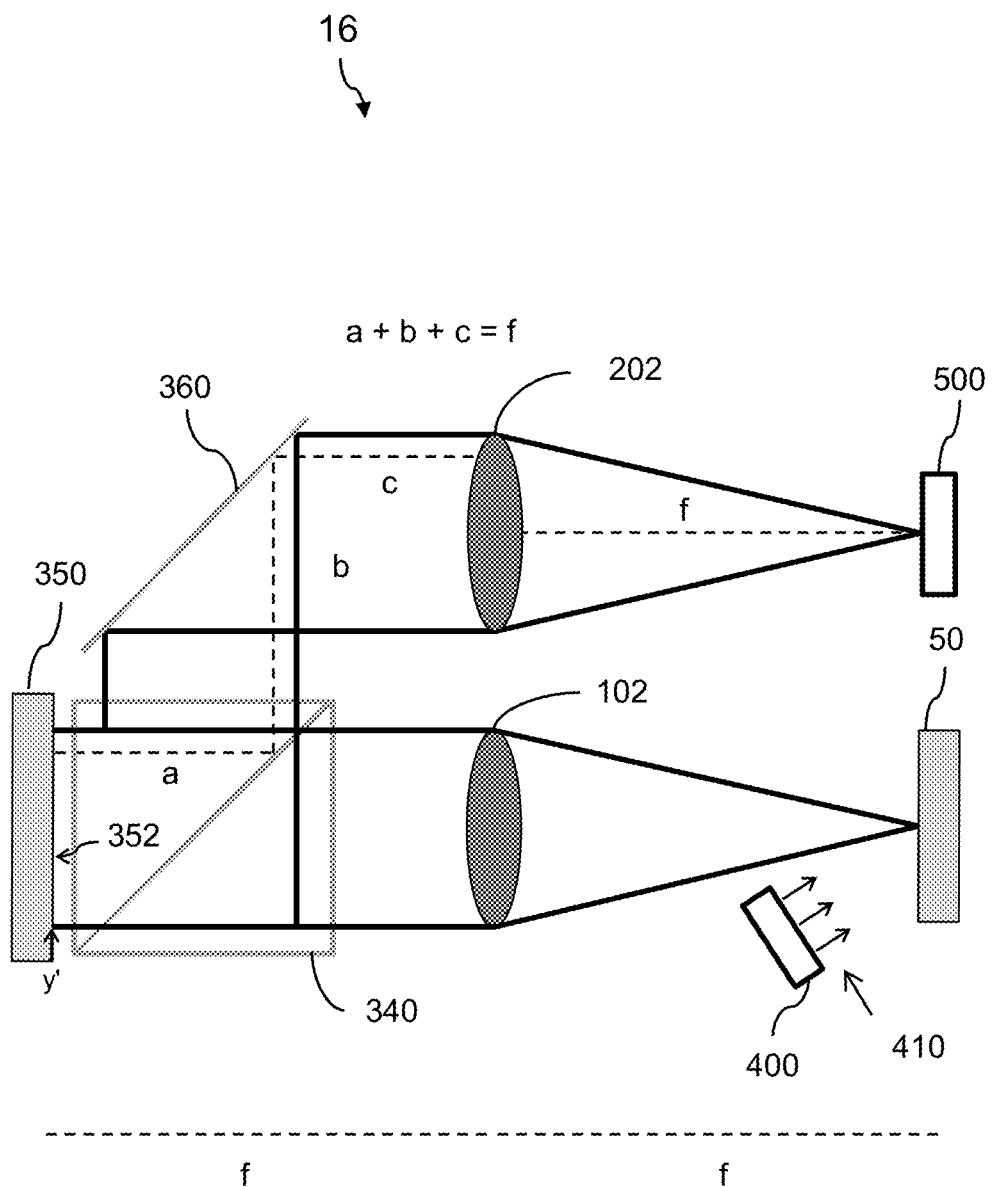
FIG. 6 is a schematic drawing of a view of components of an aperture-scanning Fourier ptychographic imaging system comprising an LCOS array.
Figure 7:
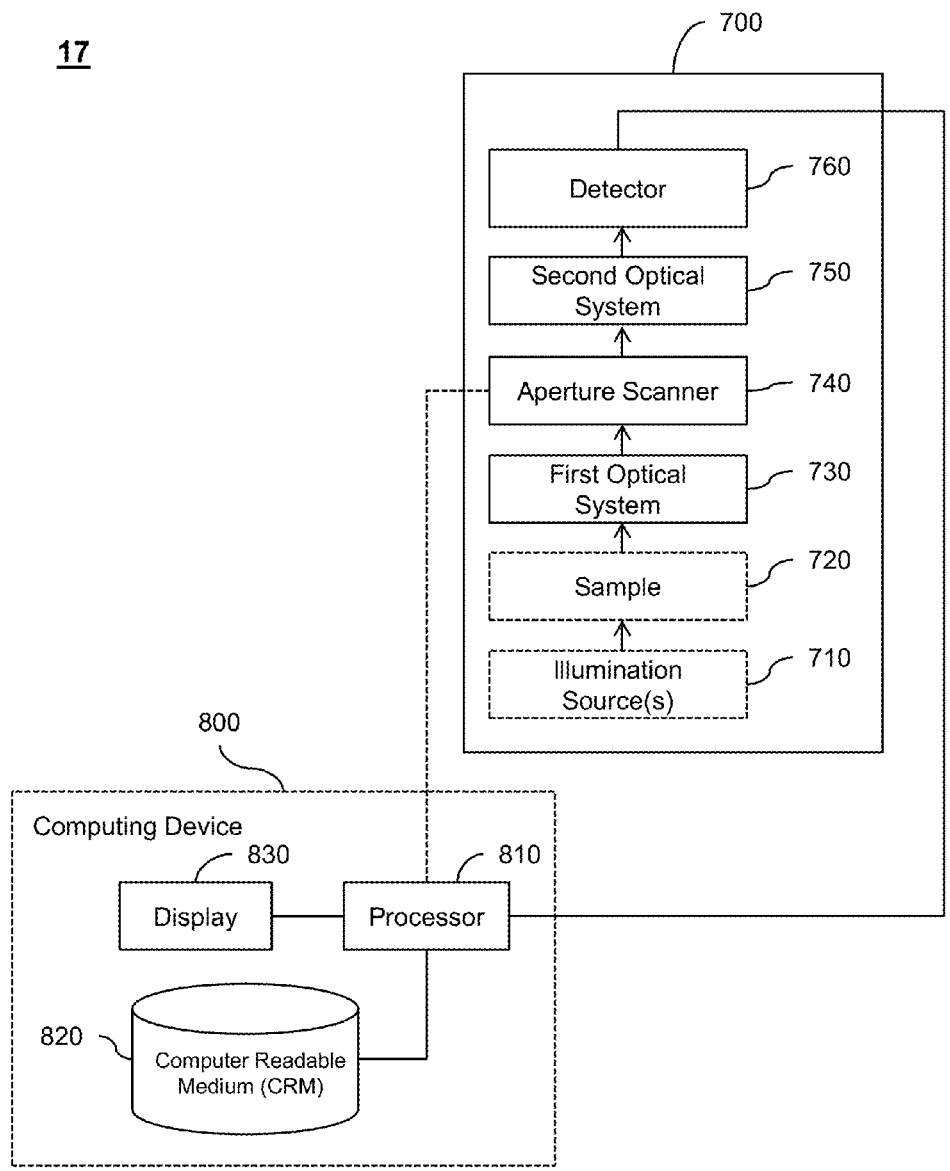
FIG. 7 is a schematic diagram of components of an aperture-scanning Fourier ptychography imaging system.

There may be similarities between certain components of the aperture-scanning Fourier ptychographic imaging system 11 in FIGS. 2A and 2B, the aperture-scanning Fourier ptychographic imaging system 12 in FIG. 3A, the aperture-scanning Fourier ptychographic imaging system 14 in FIG. 4, the aperture-scanning Fourier ptychographic imaging system 15 in FIG. 5, the aperture-scanning Fourier ptychographic imaging system 16 in FIG. 6, and the aperture-scanning Fourier ptychographic imaging system 17 in FIG. 7.

FIG. 3A is a schematic drawing of components of an aperture-scanning Fourier ptychographic imaging system 12, according to embodiments. The aperture-scanning Fourier ptychographic imaging system 12 comprises a first optical system (e.g., lens) 102 having a first focal length $f_1$ (where $f_1=f$) a second optical system (e.g., lens) 202 having a second focal length $f_2$ (where $f_1=f$), and an aperture scanner 302 in the form of a spatial light modulator. The aperture scanner 302 is configured to shift an aperture 310 to a plurality of N locations at an intermediate plane such as the Fourier plane of the sample 50. Although the aperture scanner 302 is illustrated in the form of a spatial light modulator, it would be understood that other types of aperture scanners could be used. The illustration shows the system during the image acquisition process with a sample 50 being imaged located at a sample plane. The aperture-scanning Fourier ptychographic imaging system 12 further comprises a detector 500 with a (active) detecting surface at a detector plane.

Some details of an aperture-scanning Fourier ptychographic imaging system using a spatial light modulator for shifting an aperture can be found in Horstmeyer, Roarke et al., "Overlapped Fourier coding for optical aberration removal," (2014), which is hereby incorporated by reference in its entirety.

The aperture-scanning Fourier ptychographic imaging system 12 further comprises an optional illumination source 400 that can provide illumination 410 to the sample 50. The illumination source 400 may provide a single arbitrarily patterned coherent illumination beam from any direction. Although illumination source 400 is shown in a location providing illumination 410 toward the light detector 500 in trans-illumination configuration, the illumination source 400 may be in other locations to provide illumination 410 in other directions or other components (e.g., reflective elements) may be used to direct illumination in other directions, such as, away from the next optical element, for example, the first optical system 102. Also optionally, the aperture-scanning Fourier ptychographic imaging system 11 may further comprise one or more components of a computing device comprising a processor, a display in communication with the processor, and a computer readable medium.

In FIG. 3A, the aperture-scanning Fourier ptychographic imaging system 12 is in a 4f optical arrangement with the first optical system 102 located at a distance from the second optical system 202 equal to their combined focal lengths 2f. The sample plane of the sample 50 is located at the first focal length ($f_1=f$) from the first optical system 102 and the detector plane of the detector 500 is located at an optical path distance of the second focal length (where $f_2=f$) from the second optical system 202. The Fourier plane of the sample is located at an optical path distance of the first focal length (where $f_1=f$) of the first optical system 102 away from the first optical system 102 and located at an optical path distance of the second focal length (where $f_2=f$) of the second optical system 202 away from the second optical system 202.

Figure 3B:
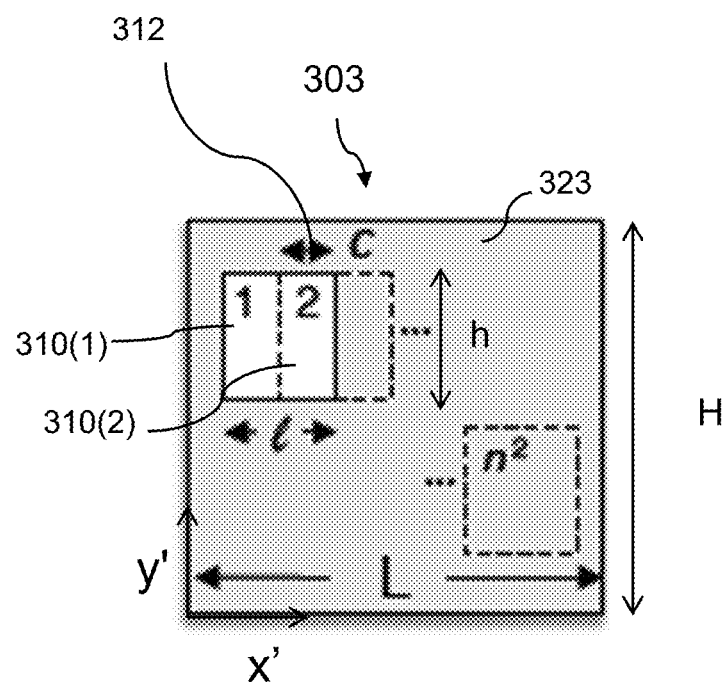
FIG. 3B is a schematic drawing of cross-sectional view of a display of a spatial light modulator that can be implemented in certain aperture-scanning Fourier ptychographic imaging systems.

FIG. 3B is a schematic drawing of cross-sectional view of an SLM display 323 of a spatial light modulator 303 that can be implemented in certain aperture-scanning Fourier ptychographic imaging systems described herein. The cross-sectional view is at a display plane of the SLM display 323. FIG. 3B includes an x'-axis and a y'-axis at the display plane.

The spatial light modulator 303 described with respect to FIG. 3B may be similar in some respects to the aperture scanner 302 described with respect to FIG. 3A.

In FIG. 3B, the SLM display 323 is a rectangular display with dimensions of width L and height H. The spatial light modulator 303 may be configured (e.g. programmed) to digitally generate on its display 323 the aperture 310 at a plurality of N locations. In this example, the plurality of N aperture locations is in the form of a 2-D rectilinear grid with equally-spaced locations (i.e. equal spacing between neighboring apertures). In other embodiments, the spacing between neighboring aperture locations may not be equally spaced and/or the aperture may have different sizes at different locations.

In FIG. 3B, the display 303 is shown at acquisition time, $t_1$, when an aperture 310(1) (shown in sold line) is generated on the SLM display 323. The illustration also includes a neighboring aperture 310(2) (shown in dotted line) that is displayed at another acquisition time (e.g., $t_2$) as denoted by a dotted line to illustrate the spatial overlapping relationship between the neighboring apertures. As shown, neighboring apertures 310(1), 310(2) have an overlap 312 in the x'-direction of a distance c.

In some cases, the overlap 312 may be at least about 70% of the area of the aperture 310. In other cases, the overlap 312 may be at least about 75% of the area of the aperture 310. In other cases, the overlap 312 may be between 2-90% of the area of the aperture 310. Display instructions may be used by the SLM 303 to generate an aperture on the display 323 in the rectilinear grid.

The overlap 312 between neighboring (adjacent) apertures may correspond to setting the n>L/l. For example, if n=9, setting L/l=2.5 will generate an overlap between neighboring apertures of more than 75%. Both apertures 310(1) and 310(2) have a constant rectangular shape with a width l and height of h. In other embodiments, the aperture 310 displayed at different locations may have different sizes and/or shapes.

In FIG. 3B, the SLM display 303 has a 2-D rectilinear grid with square dimensions (n×n dimensions). In this case, the N aperture locations are described as $(X_i, Y_j)$, i=1 to n, j=1 to n, in the display plane and the number of aperture locations, $N=n^2$. Typically, the aperture 310 may be displaced from the origin of this 2-D rectilinear grid by a two-dimensional vector $c_j=(c_{xj}, c_{yj})$ for $1<j<n^2$. In this configuration, a light detector can capture at the detector plane M different intensity images, $I_{k,l}$, (M=k×l) at different aperture locations and corresponding acquisition times.

FIGS. 4-6 are schematic drawings illustrating examples of different configurations of the components of the aperture-scanning Fourier ptychographic imaging system 12 described with reference to FIG. 3A.

FIG. 4 is a schematic drawing of components of an aperture-scanning Fourier ptychographic imaging system 14, according to certain aspects. The aperture-scanning Fourier ptychographic imaging system 14 comprises a first optical system (e.g., lens) 102 having a first focal length $f_1=f$, a second optical system (e.g., lens) 202 having a second focal length $f_2=f$, and a detector 500. The aperture-scanning Fourier ptychographic imaging system 14 further comprises an aperture scanner comprising a DMD array 320 having a display surface 322 and a sequence of one or more mirrors 330 having a reflective surface 332. The surface 322 includes a y'-axis and an x'-axis (not shown) orthogonal to the y'-axis, both in the plane at the surface 322. The illustrated example is shown with a sample 50 being imaged at a sample plane.

The aperture-scanning Fourier ptychographic imaging system 14 also comprises an optional illumination source 400 configured to provide illumination 410 to the sample 50 during an image acquisition process as shown in the illustration. In this illustrated example, the illumination source 400 is shown located (e.g., between first optical system 102 and the sample 50) to direct illumination 410 away from the first optical system 102. In the configuration, the first optical system 102 can receive light reflected from the sample surface or emitted from the sample 50. The illustrated configuration can be used in luminescence imaging applications. In other examples, the illumination source 400 may be in other locations and/or direct illumination in other directions. Although a single illumination source 400 is shown in this example, multiple illumination sources may be used.

The aperture-scanning Fourier ptychographic imaging system 14 is in a 4f optical arrangement with the first optical system 102 located at an optical path distance from the second optical system 202 equal to their combined first and second focal lengths 2f. The sample plane is located at an optical path distance of the first focal length $f_1$=f from the first optical system 102.

In this 4f arrangement, the detector plane is located at an optical path length of the second focal length $f_2$=f from the second optical system 202. The DMD array 320 is located at an optical path length of the first focal length $f_1$=f away from the first optical system 102. The sequence of one or more mirrors 330 is located at an optical path length, b, from the DMD array 320 and at an optical path length, a, from the second optical system 202. The combined optical path distance between the DMD array 320 and the second optical system 202 is a+b=f. The Fourier plane of the sample is located at an optical path length of the first focal length $f_1$=f of the first optical system 102 away from the first optical system 102 and located at a combined optical path length a+b=f from the second optical system 202. In FIG. 4, a sample 50 being imaged is shown located at the sample plane, the detector is located so that the active detecting surface is at the detector plane, and aperture scanner 320 is located so that the display surface 322 is at the Fourier plane associated with the sample plane of the sample 50.

The DMD array 320 is configured to shift an aperture to a plurality of N aperture locations at the Fourier plane of the sample 50. The DMD array 320 comprises a plurality of micromirrorrs. The DMD array 320 generates an aperture at each aperture location at the display surface by rotating a corresponding set of one or more micromirrors of the DMD array 320 to reflect incident light at an angle, a, directed to the one or more mirrors 330. In some cases, other surrounding micromirrors in the DMD array 320 are oriented at an angle that reflects incident light away from the one or more mirrors 330.

In FIG. 4, the one or more mirrors 330 are configured to receive light reflected by the aperture generated by the DMD array 320 to second optical system 202. In some aspects, the sequence of one or more mirrors 330 may be configured to correct the differences in optical path length at the different locations along the y'-axis to the surface of the mirrors 330. The illustration indicates an optical path b of a center ray between the surface 322 of the DMD array 320 and the surface 332 of the mirror(s) 330 and the optical path length a between the mirror(s) 330 and the second optical system 202. The combined optical path of the center ray between first optical system 102 and the second optical system is a+b=f. However, the optical path distance between the sequence of mirrors 330 and the DMD array 320 is not the same from edge to edge of these devices. To correct these differences, the sequence of one or more mirrors 330 may have locations and/or orientations that correct for these differences. For example, a binary grating pattern (i.e., a blazed grating) may be super-imposed on top of the sub-aperture pattern displayed on the DMD. Alternatively, an algorithm similar to the simulated annealing correction approach discussed in Horstmeyer, Roarke et al., "Overlapped Fourier coding for optical aberration removal," (2014) may be used to find an arbitrarily-shaped pattern of mirrors to offer optimized correction performance. This reference is hereby incorporated by reference in its entirety for details of this approach.

Although not shown, the aperture-scanning Fourier ptychographic imaging system 14 may also include one or more components of a computing device, which comprises a processor, a display in electrical communication with the processor, and a computer readable medium in electrical communication with the processor.

FIG. 5 is a schematic drawing of components of an aperture-scanning Fourier ptychographic imaging system 15, according to certain aspects. The aperture-scanning Fourier ptychographic imaging system 15 comprises a first optical system (e.g., lens) 102 having a first focal length $f_1$=f, a second optical system (e.g., lens) 202 having a second focal length $f_2$=f, and a detector 500. The aperture-scanning Fourier ptychographic imaging system 14 further comprises an aperture scanner in the form of a DMD array 320 having a display surface 322. The surface 322 includes a y'-axis and an x'-axis (not shown) orthogonal to the y'-axis, both in the plane at the surface 322. The illustrated example is shown with a sample 50 being imaged at a sample plane.

The aperture-scanning Fourier ptychographic imaging system 15 also comprises an optional illumination source 400 configured to provide illumination 410 to the sample 50 during an image acquisition process as shown in the illustration. For example, illumination source 400 may provide a single arbitrarily patterned coherent illumination beam from any direction. In this illustrated example, the illumination source 400 is shown located (e.g., between first optical system 102 and the sample 50) to direct illumination 410 away from the first optical system 102. In the configuration, the first optical system 102 can receive light reflected from the sample surface or emitted from the sample 50. The illustrated configuration can be used in luminescence imaging applications. In other examples, the illumination source 400 may be in other locations and/or direct illumination in other directions. Although a single illumination source 400 is shown in this example, multiple illumination sources may be used.

In this configuration, the angle, θ, between the center ray optical paths between first optical system 102 and the DMD array 320 and the second optical system 202 and the DMD array 320 is small angle. Since the angle, θ, is small in this configuration, the optical path distances for these center rays can be approximated as parallel and of equal distances. In one case, the angle, θ, may be between about 1 degree and about 10 degrees. In another case, the angle, θ, is about 10 degrees. In another case, the angle, θ, is about 15 degrees.

With this above-discussed approximation, the aperture-scanning Fourier ptychographic imaging system 14 is approximated as a 4f optical arrangement with the first optical system 102 located at an optical path distance from the second optical system 202 that is approximated as equal to the combined first and second focal lengths 2f. The sample plane is located at the first focal length $f_1$=f from the first optical system 102 and the detector plane is located at the second focal length $f_s=f$ from the second optical system 202. The Fourier plane of the sample is located at an optical path length of the first focal length $f_1=f$ of the first optical system 102 away from the first optical system 102 and located at an optical path length of approximately the second focal length $f_2=f$ of the second optical system 202 away from the second optical system 202.

In FIG. 5, a sample 50 being imaged is shown located at the sample plane and the detector 500 is located so that the active detecting surface is approximately at the detector plane. The DMD array 320 is located at an optical path length of the first focal length $f_1=f$ away from the first optical system 102 and located at an optical path length of approximately the second focal second focal length $f_2=f$ from the second optical system 202.

The DMD array 320 is configured to shift an aperture to a plurality of N aperture locations at the Fourier plane of the sample 50. The DMD array 320 comprises a plurality of micromirrorrs. The DMD array 320 generates an aperture at each aperture location at the display surface by rotating a corresponding set of one or more micromirrors of the DMD array 320 to reflect incident light at an angle, a, directed to the second optical system 202. In some cases, other surrounding micromirrors in the DMD array 320 are oriented at an angle that reflects incident light away from the second optical system 202.

Although not shown, the aperture-scanning Fourier ptychographic imaging system 14 may also include one or more components of a computing device, which comprises a processor, a display in electrical communication with the processor, and a computer readable medium in electrical communication with the processor.

FIG. 6 is a schematic drawing of a view of components of an aperture-scanning Fourier ptychographic imaging system 16, according to certain aspects. The aperture-scanning Fourier ptychographic imaging system 16 comprises a first optical system (e.g., lens) 102 having first optical system (e.g., lens) 102 having a first focal length $f_1=f$, a second optical system (e.g., lens) 202 having a second focal length $f_2=f$, and a detector 500. The aperture-scanning Fourier ptychographic imaging system 16 further comprises an aperture scanner. In this illustrated example, the aperture scanner comprises a beam splitter 340, a LCOS array 350 having a display surface 352, and a mirror 360. The surface 352 includes a y'-axis and an x'-axis (not shown) orthogonal to the y'-axis.

The aperture-scanning Fourier ptychographic imaging system 16 also comprises an optional illumination source 400 configured to provide illumination 410 to the sample 50 during an image acquisition process as shown in the illustration. In this illustrated example, the illumination source 400 is shown located (e.g., between first optical system 102 and the sample 50) to direct illumination 410 away from the first optical system 102. In the configuration, the first optical system 102 can receive light reflected from the sample surface or emitted from the sample 50. The illustrated configuration can be used in luminescence imaging applications. In other examples, the illumination source 400 may be in other locations and/or direct illumination in other directions. Although a single illumination source 400 is shown in this example, multiple illumination sources may be used.

The aperture-scanning Fourier ptychographic imaging system 16 is in a 4f optical arrangement with the first optical system 102 located at an optical path distance from the second optical system 202 equal to their combined first and second focal lengths 2f. The sample plane is located at an optical path distance of the first focal length $f_1 f$ from the first optical system 102. In this 4f arrangement, the detector plane is located at an optical path length of the second focal length $f_2=f$ from the second optical system 202. The LCOS array 350 is located at an optical path length of the first focal length $f_1 f$ away from the first optical system 102.

The beam splitter 340 is configured to pass incident light of first wavelength(s) received from the first optical system 102 and to absorb/reflect incident light of second wavelength(s) received from the first optical system 102. For example, the beam splitter 340 may be configured to pass incident light of wavelengths associated with emissions from fluorophore in a sample illuminated by excitation illumination in a fluorescent imaging application. The beam splitter 340 is further configured to absorb incident light of the second wavelength(s) received from the LCOS array 350, and reflect incident light of the first wavelength(s) received from the LCOS array 350 to the mirror 360. Alternatively, a conventional beam splitter may be used with the addition of a spectral filter placed anywhere in the optical path between the sample and the detector, which can pass light of wavelengths associated with emissions from fluorophore and absorb excitation illumination in a fluorescent imaging application.

In FIG. 6, the optical path distance between the LCOS array 350 and the beam splitter 340 is designated as, a. The optical path distance between the beam splitter 340 and the mirror 360 is b. The optical path distance between the mirror 360 and the second optical system 202 is c. The combined optical path distance between the LCOS array 350 and the second optical system 202 is a +b+c=f. The Fourier plane of the sample in this optical arrangement is at an optical path length of the first focal length $f_1=f$ from the first optical system 102 and located at a combined optical path length a +b+c=f from the second optical system 202. In FIG. 4, a sample 50 being imaged is shown located at the sample plane, the detector 500 is located so that the active detecting surface is at the detector plane, and display surface 352 of the LCOS array 350 is located at the Fourier plane associated with the sample plane.

Advantages of this configuration may be that the optical path is of equal length between the first and second optical systems 102 and 202 and that the optical elements do not need to be placed at challenging angles.

The LCOS array 350 is configured to shift an aperture to a plurality of N aperture locations at an intermediate plane, which in this case is the Fourier plane associated with the sample plane. The LCOS array 350 comprises display comprised of a plurality of display elements that can be set to be reflective. The LCOS array 350 generates an aperture at each aperture location at the display surface by setting one or more display elements to be reflective in order to reflect incident light back to the beam splitter 340. In some cases, the surrounding elements are set to be substantially transmissive or absorbtive.

Although certain aperture-scanning Fourier ptychographic imaging systems are described as configured to generate an aperture at an intermediate plane, a plurality of apertures may be generated instead.

Although not shown, the aperture-scanning Fourier ptychographic imaging system 16 may also include one or more components of a computing device, which comprises a processor, a display in electrical communication with the processor, and a computer readable medium in electrical communication with the processor.

IV. Aperture-Scanning Fourier Ptychographic Imaging System

In certain aspects, an aperture scanning Fourier ptychographic system comprises a first optical system (e.g., first lens), an aperture scanner configured to generate an aperture at a plurality of N aperture locations at an intermediate plane, a second optical system (e.g., second lens), and a radiation detector configured to capture a plurality of M intensity images. Optionally, the aperture scanning Fourier ptychographic system may further comprise an illumination source for providing illumination and/or a processor. In some cases, the illumination source may provide a single arbitrarily patterned coherent illumination beam from any direction. In certain aspects, the first optical system, second optical system, radiation detector, and sample plane of the sample are arranged in a 4-f optical arrangement. During an image acquisition process, the illumination source illuminates a sample placed at a sample plane. The first optical system receives light from the sample and the aperture scanner generates an aperture at a plurality of locations at the Fourier plane of the sample. There is an overlapping area between apertures at certain adjacent locations of the plurality of N aperture locations. The second optical system receives light through the aperture. The radiation detector receives light from the second optical system as modulated by the aperture at the different locations. The radiation detector captures a plurality of M intensity images corresponding to different aperture locations of the plurality of N aperture locations. During a recovery process, a processor iteratively stitches together the M overlapping intensity images in Fourier space to recover a wide-field, complex image of the sample. In certain aspects, the aperture scanning Fourier ptychographic system can also digitally adjust the complex higher-resolution image to accommodate for defocus and correct aberrations in its optical elements. In certain cases, the aperture scanning Fourier ptychographic system can also digitally propagate the complex image to other planes, for example, to generate a three-dimensional image.

Although this aperture-scanning Fourier ptychographic imaging system is described as configured to generate an aperture at an intermediate plane, this system in another case could generate a plurality of apertures at the intermediate plane.

Aperture scanning Fourier ptychographic methods performed by aperture scanning Fourier ptychographic systems described herein comprise an acquisition process, a recovery process, and an optional display process. During the acquisition process, the aperture scanner generates an aperture at a plurality of N aperture locations and the radiation detector captures at M sample times ($t_i$, i=1 to M) a plurality of M intensity images corresponding to different aperture locations. During the recovery process, one or more complex images are determined using the plurality of M intensity images. During the optional display process, the recovered complex images and other output is provided on a display. In some cases, M=N.

FIG. 7 is a schematic diagram of components of an aperture scanning Fourier ptychographic system 17, according to embodiments. The aperture scanning Fourier ptychographic system 17 comprises an aperture scanning Fourier ptychographic device 700 and optionally one or more components of a computing device 800. The aperture scanning Fourier ptychographic device 700 comprises a first optical system 730 (e.g., first objective lens) configured to receive light from the sample 720, an aperture scanner 740 configured to generate an aperture at a plurality of N aperture locations in an intermediate plane (e.g., Fourier plane of sample 720), a second optical system 750 (e.g., second objective lens) for receiving light through the aperture, and a detector 760 for capturing M intensity images based on incident light from the second optical system 750.

The aperture scanning Fourier ptychographic device 700 further comprises an optional (denoted by dotted line) illumination source 710 configured to provide illumination to a sample 720. In this illustration, the sample 720 is provided to the aperture scanning Fourier ptychographic device 700 during an acquisition process as denoted by the dotted line. In other cases, the sample 720 is not included. In some cases, the illumination source 710 may provide a single coherent illumination beam from any direction. The computing device 800 comprises a processor 810 (e.g., a microprocessor), a computer readable medium (CRM) 820 in electrical communication with the processor 810, and a display 830 in electrical communication with the processor 810. The processor 810 of the computing device 800 is also in electrical communication with the detector 760 of the aperture scanning Fourier ptychographic device 700. In certain cases, the processor 810 may also be in electrical communication with the aperture scanner 740. In one case, for example, the processor 810 may be in electrically communication with the aperture scanner 740 and the light detector 760 to synchronize aperture generation with image acquisition. The computing device 800 can be in various forms such as, for example, a smartphone, laptop, desktop, tablet, etc. Various forms of computing devices would be contemplated by one skilled in the art.

During a measurement process, the aperture scanner 740 generates an aperture at a plurality of N aperture locations, $(X_i, Y_j)$, i=1 to m, j=1 to n, in a plane (e.g., Fourier plane of the optical arrangement). The first optical system 730 receives incident light propagating from the surface of the sample 720. The second optical system 750 receives light as modulated by the aperture. The detector 760 receives and measures the intensity distribution of light propagated by the second optical system. The detector 760 captures or acquires an intensity distribution $I_{i,j}$, i=1 to o, j=1 top at M (=o×p) sample times, $t_{i=1\ to\ M}$, to capture a plurality of M intensity images of the sample 720. In one aspect, each of the M intensity images corresponds to a different aperture location of the plurality of N aperture locations.

In certain aspects, one or more of the full field-of-view intensity images captured by an aperture scanning Fourier ptychographic system described herein may be divided into one or more tile images. In these cases, the processor may construct a higher resolution complex image for each tile independently, and then combine the tile images to generate the full field-of-view image. This ability to process tile images independently allows for parallel computing. In these aspects, each tile may be represented by a two-dimensional area. In polar spatial coordinates, each tile may be a circular area or an oval area. In rectilinear spatial coordinates, the full field-of view low resolution image may be divided up into a two-dimensional matrix of tiles in a rectangular area. In some embodiments, the dimensions of a two-dimensional square matrix of tiles may be in powers of two when expressed in number of pixels of the radiation sensor such as, for example, a 256 by 256 matrix, a 64×64 matrix, etc.

In FIG. 7, the processor 810 is in electronic communication with detector 760 to receive signal(s) with the image data corresponding to M intensity images. The image data may include, for example, intensity distributions, associated acquisition times, etc. During a recovery process, the processor 810 can iteratively "stitch" together the plurality of M intensity images in Fourier space to recover a wide-field, complex image of the sample 720 at the sample plane. In certain aspects, the processor 810 can also digitally refocus the complex image to accommodate for any defocus of the sample and/or aberrations in the system. In certain aspects, the processor 810 can also propagate the complex image to one or more planes. The image data from these propagated complex images at different planes can be used to generate a three-dimensional image. In certain aspects, the processor 810 can also generate a complex image at different illumination wavelengths (RGB) to generate a complex color image.

The processor 810 is in electronic communication with CRM 820 (e.g., memory) to communicate signals with image data to store/to/from the CRM 820. Processor 810 is shown in electronic communication with display 830 to be able to send image data and instructions to display the wide-field, complex image of the sample and other output, for example, to a user of the aperture scanning Fourier ptychographic system 17. As used herein, electronic communication between components of aperture scanning Fourier ptychographic system 17 may be in wired or wireless form.

The processor 810 (e.g., microprocessor) may also execute instructions stored on the CRM 820 to perform one or more functions of aperture scanning Fourier ptychographic system. For example, the processor 810 may execute instructions to perform one or more steps of the recovery process of the aperture scanning Fourier ptychographic method. As another example, the processor 810 may execute instructions for generating an aperture at the plurality of aperture locations. As another example, the processor 810 may execute instructions stored on the CRM 820 to perform one or more other functions of the aperture scanning Fourier ptychographic system such as, for example, 1) interpreting image data from the plurality of intensity images, 2) generating a higher resolution complex image from the image data, and 3) displaying one or more images or other output from the aperture scanning Fourier ptychographic method on the display 830.

The CRM (e.g., memory) 820 can store instructions for performing some of the functions of the aperture scanning Fourier ptychographic system. The instructions are executable by the processor 810 or other processing components of the aperture scanning Fourier ptychographic system. The CRM 820 can also store the (lower resolution) intensity and higher resolution complex images, and other data produced by the aperture scanning Fourier ptychographic system.

The aperture scanning Fourier ptychographic system also includes a display 830 in electronic communication with the processor 810 to receive data (e.g., image data) and provide output data (e.g., images) to an operator of the aperture scanning Fourier ptychographic system. The image display 830 may be a color display or a black and white display. In addition, the display 830 may be a two-dimensional display or a three-dimensional display. In one embodiment, the display 830 may be capable of displaying multiple views.

Modifications, additions, or omissions may be made to the aperture scanning Fourier ptychographic system 17 or aperture scanning Fourier ptychographic device 700 without departing from the scope of the disclosure. In addition, the components of aperture scanning Fourier ptychographic system 17 or the aperture scanning Fourier ptychographic device 700 may be integrated or separated according to particular needs. For example, the computing device 800 or components thereof may be integrated into the aperture scanning Fourier ptychographic device 700. In some embodiments, the processor 810 or other suitable processor may be part of the aperture scanning Fourier ptychographic device 700. In some cases, the processor 810 may be integrated into the radiation detector 760 so that the radiation detector 760 performs the functions of the processor 810. As another example, the CRM 820 and/or display 830 may be omitted from the aperture scanning Fourier ptychographic system 17 in certain cases.

For simplicity, the first and second optical systems (e.g. first and second lenses) of certain aperture-scanning Fourier ptychographic imaging systems herein are described having the same focal length, f, in a 4f optical arrangement. It will be understood that the first optical system can have a different focal length than the second optical system. For example, the first optical system may have a first focal length of $f_1$ that is different that the second focal length $f_2$ of the second optical system. In this case, the sample plane is located at a distance of first focal length $f_1$ from the first optical system, the detector plane will be at a distance of the second focal length $f_2$ from the second optical system, and the Fourier plane will be at a distance of $f_1$ from the first optical system and a distance of $f_2$ from the second optical system.

In many aspects described herein, the aperture can be generated at a plurality of N aperture locations in a Fourier plane of the sample. However, it would be understood that the aperture could be generated in another intermediate plane conjugate to the sample such as, for example, the aperture plane of a compound lens system or the back-focal plane of a microscope objective.

In certain aspects, an aperture scanning Fourier ptychographic system may further comprise a receptacle for receiving the sample at a sample surface. The sample surface may be part of a component of or a separate component of the aperture scanning Fourier ptychographic system.

IV. Aperture-Scanning Fourier Ptychographic Imaging Methods

In certain aspects, an aperture scanning Fourier ptychographic method comprises an acquisition process, a recovery process, and an optional display process. In the acquisition process, a plurality of M intensity lower resolution images are acquired, each intensity image corresponding to a different aperture location at the intermediate plane of the aperture scanning Fourier ptychographic system. Each intensity image is based on an intensity (amplitude) distribution measured at the detector plane at a particular acquisition time, $t_{i=1\,to\,M}$. The light detector measures incident light received from the second optical system, which receives light from the aperture.

Figure 8:
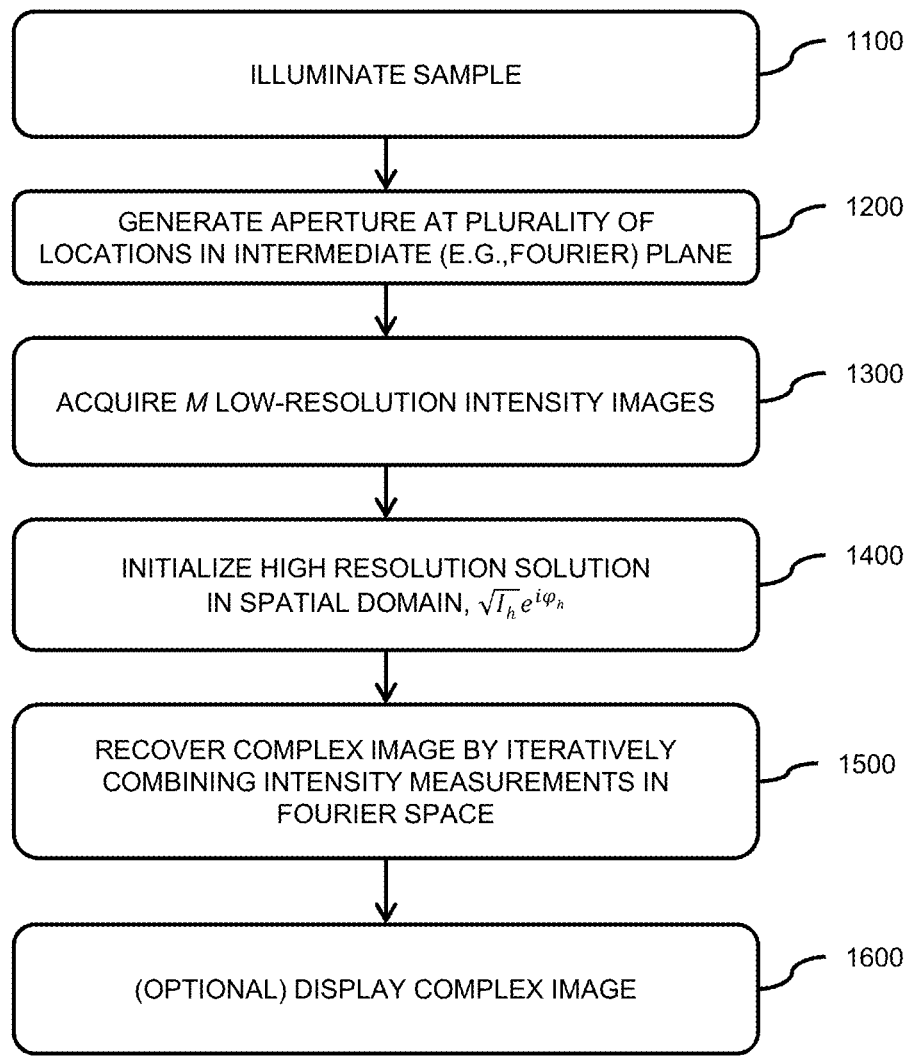
FIG. 8 is a flowchart of an aperture-scanning Fourier ptychography imaging method performed by an aperture-scanning Fourier ptychography imaging system.
Figure 9A:
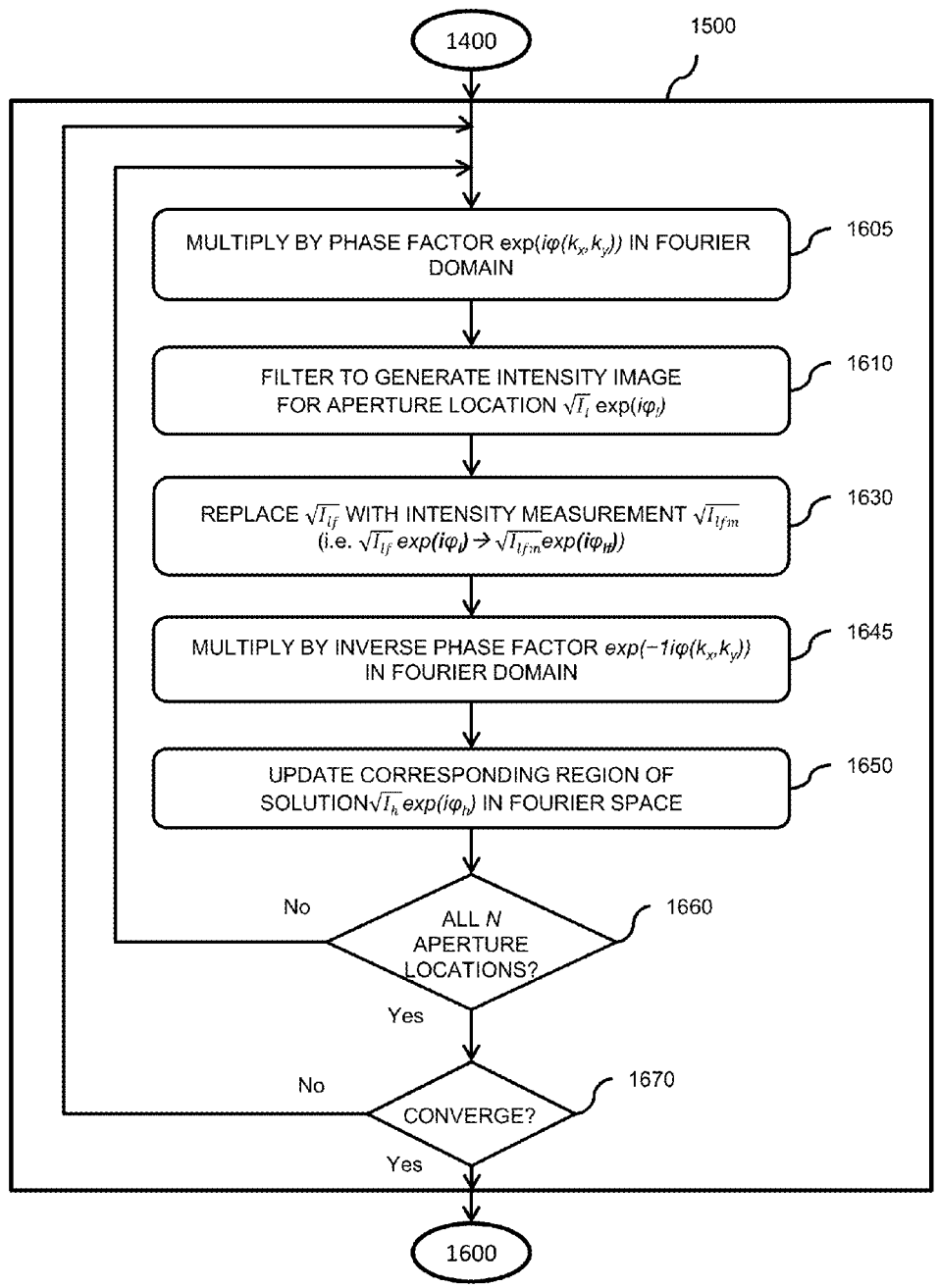
FIG. 9A is a flowchart of an example of sub-steps of one or more steps of the method of FIG. 8.
Figure 9B:
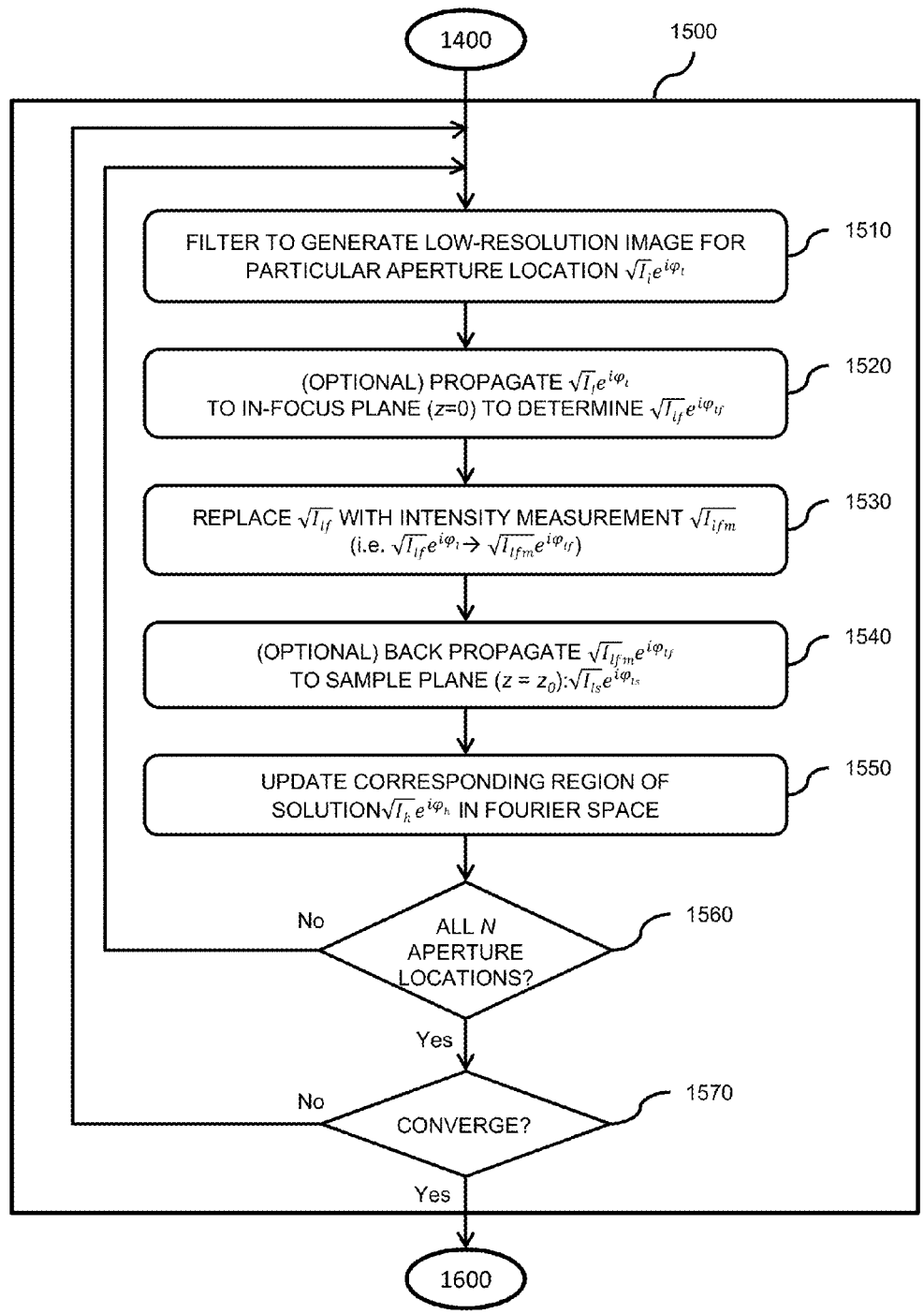
FIG. 9B is a flowchart of another example of sub-steps of one or more steps of the method of FIG. 8.

In FIGS. 8, 9A and 9B and their associated description, subscript "h" refers to higher resolution, complex image, subscript "l" refers to lower resolution intensity, subscript "f" refers to focused position, subscript "m" refers to measured, and subscript "s" refers to sampled.

FIG. 8 is a flowchart of an aperture scanning Fourier ptychographic method performed by an aperture scanning Fourier ptychographic system. The aperture scanning Fourier ptychographic method comprises an acquisition process (steps 1100, 1200, and 1300), a recovery process (steps 1400 and 1500), an optional propagation step and an optional display process (step 1600).

At step 1100, the illumination source provides illumination to a sample during M sample times $t_{i=1\,\ldots\,M}$. The first optical system receives incident light from the sample. In certain cases, the illumination source may provide illumination of different wavelengths at different sample times.

For example, the illumination source may provide RGB illumination of three wavelengths $\lambda_1$, $\lambda_2$, and $\lambda_3$ corresponding to red, green, blue colors, respectively, for a color imaging implementation. In luminescence imaging examples, the illumination source may provide illumination that is of wavelength(s) for exciting fluorophore in the sample. In these examples, the illumination source may be located and directed to provide illumination directed away from the next element in the optical arrangement. For example, the illumination source may be directed away from the first optical system.

At step 1200, an aperture scanner generates an aperture (or plurality of apertures) at a plurality of N aperture locations, $(X_i, Y_j)$, i=1 to m, j=1 to n, in an intermediate (e.g., Fourier) plane of the optical arrangement. The aperture scanner may generate the aperture at the different locations based on instructs that define the order of the aperture locations. These instructions may be implemented with a processor and may be stored on computer readable medium. The wave vector in x and y directions can be denoted as $k_{xi}$, and $k_{yi}$. The second optical system may receive incident light as modulated by the aperture. In some cases, the neighboring apertures in the plurality of aperture locations have an overlapping region.

The detector receives and measures the intensity distribution of light propagated by a second optical system receiving incident light from the aperture. At step 1300, the radiation detector acquires a snapshot intensity distribution measurement at each of the M sample times, $t_{i=1 to M}$ to acquire a plurality of M intensity images $I_{i,j}$, i=1 to o, j=1 top where M=o×p. Each of the M intensity images acquired by the light detector corresponds to a different aperture location of the plurality of N aperture locations. Each of the M intensity images acquired by the light detector is also associated with a region in Fourier space. In certain aspects, there are overlapping areas between neighboring regions in Fourier space. In one embodiment, there is an overlapping area between neighboring regions of 2% to 99.5% of the area of one of the regions. In another embodiment, there is an overlapping area between neighboring regions of 65% to 75% of the area of one of the regions. In one embodiment, there is an overlapping area between neighboring regions of about 65% of the area of one of the regions.

At steps 1400 and 1500, a higher (i.e. improved) resolution, complex image of the sample is recovered based on the plurality of M intensity distribution measurements, $I_{i,j}$, i=1 to o, j=1 captured at step 1300.

At step 1400, a higher resolution complex image: $\sqrt{I_h}e^{i\varphi_h}$ is initialized in the spatial domain, and a Fourier transform is applied to the initial value to obtain an initialized Fourier transformed image $\tilde{I}_h$. The initialized higher-resolution solution may be an initial guess. In some cases, the initial guess may be determined as a random complex matrix (for both intensity and phase). In other cases, the initial guess may be determined as an interpolation of the intensity distribution measurement with a random phase. An example of an initial guess is $\varphi=0$ and $I_h$ interpolated from any intensity image of the sample area. Another example of an initial guess is a constant value. The Fourier transform of the initial guess can be a broad spectrum in the Fourier domain.

At step 1500, the higher-resolution image of the sample area is computationally constructed by iteratively combining intensity measurements in Fourier space using a processor, which may be part of or a separate component of the of the an aperture scanning Fourier ptychographic system.

At an optional step 1600, a display may receive image data such as a higher resolution complex image data and/or other data from the processor, and display the data on the display.

Although an aperture scanning Fourier ptychographic system may not directly measure phase information, the aperture scanning Fourier ptychographic system may determine this data during its recovery process. The phase data can be used to generate a complex image of the sample. In addition, certain aperture scanning Fourier ptychographic methods can use phase information for aberration correction. For example, certain aperture scanning Fourier ptychographic methods introduces a phase map to the coherent optical transfer function to compensate for aberrations at the pupil plane during the iterative image recovery process. Examples of image recovery processes are described with reference to FIGS. 9A and 9B discussed in the following sections.

A) Digital Re-Focusing and Wavefront Correction

Consider a situation where a sample being imaged is illuminated by a light field. The optical transmission exiting the sample surface includes both amplitude and phase spatial variations. In a conventional bright field microscope, this light field is collected and refocused to form an image of the sample at the image plane. Conventional light sensors and the human eye can only detect amplitude (intensity) variations, but not the phase variations.

There are advantages to imaging platforms that can collect both the amplitude and phase variations at the image plane and connect that data back to the optical transmission exiting the sample surface. For example, this set of amplitude and phase data can be used to perform computational refocusing, which allows for imaging at any given plane below the sample's surface. As another example, this set of amplitude and phase data can be used to correct for optical aberrations in optical imaging systems. Optical aberrations present physical limitations that may prevent certain imaging systems from performing at their theoretical resolution dictated by general optical principles. For example, a camera with a 50 mm lens (e.g., a Nikon Nikkor 50 mm f/1.2) having a field of view of over 1 cm diameter and a numerical aperture (NA) of about 0.4, should theoretically be capable of imaging with sub-micron optical resolution, but optical aberrations limit it to 10's microns resolution.

FIG. 9A is a flowchart illustrating an example of sub-steps, one or more of which may be included in step 1500 of the aperture scanning Fourier ptychographic method of FIG. 8. One or more of these steps may be performed by a processor (e.g., processor 810) of the aperture scanning Fourier ptychographic system. The illustrated flowchart includes optional digital wavefront correction steps 1605 and 1645. Step 1605 provides a connection between the actual sample profile and the captured intensity data (which may include aberrations) with multiplication of a pupil function: $e^{i\varphi(k_x,k_y)}$. Step 1645 inverts this connection to determine an aberration-free reconstructed complex image of the sample.

Sample defocus can be implemented by introducing the defocus phase factor to the pupil plane (i.e., a defocus aberration):

$$e^{i\varphi(k_x,k_y)} = e^{i\sqrt{(2\pi/\lambda)^2 - k_x^2 - k_y^2} \cdot z_0}, \quad \text{(Eqn. 4)}$$

$$k_x^2 + k_y^2 < (NA \cdot 2\pi/\lambda)^2$$

where $k_x$ and $k_y$ are the wavenumbers at the pupil plane, $z_0$ is the defocus distance, and NA is the numerical aperture of an optical element (e.g., first optical system and/or second optical system).

At step 1605, the initial complex, higher resolution Fourier transformed image $\tilde{I}_h$ is multiplied by a phase factor $e^{i\varphi(k_x,k_y)}$ or $\exp(i\varphi(k_x,k_y))$ in the Fourier domain.

At step 1610, low-pass filtering of the higher-resolution image $\sqrt{I_h}e^{i\varphi_h}$ in the Fourier domain is performed to generate a lower resolution intensity image $\sqrt{I_l}e^{i\varphi_l}$ or $\sqrt{I_l}\exp(i\varphi_l)$ for an aperture location associated with a wave vector $(k_x^i, k_y^i)$. The Fourier transform of the higher-resolution image is $\tilde{I}_h$ and the Fourier transform of the lower resolution intensity image for a particular aperture location is $\tilde{I}_l$. In the Fourier domain, the aperture scanning Fourier ptychographic method filters the low-pass region from the spectrum $\tilde{I}_h$ of the higher-resolution image $\sqrt{I_h}e^{i\varphi_h}$. In some cases, this low-pass region may be a circular aperture with a radius of $NA*k_0$, where $k_0$ equals $2\pi/\lambda$ (the wave number in vacuum), given by the coherent optical transfer function of an optical system (e.g., first optical system and/or second optical system). In Fourier space, the location of the low-pass region corresponds to a particular aperture location in the spatial domain.

At step 1630, the computed amplitude component $\sqrt{I_{lf}}$ of the intensity image at the in-focus plane, $\sqrt{I_{lf}}e^{i\varphi_{lf}}$, is replaced with the square root of the intensity measurement $\sqrt{I_{lfm}}$ measured by the light detector of the aperture scanning Fourier ptychographic system. This forms an updated lower resolution target: $\sqrt{I_{lfm}}e^{i\varphi_{lf}}$.

At step 1645, the updated lower resolution target: $\sqrt{I_{lfm}}e^{i\varphi_{lf}}$ is multiplied by an inverse phase factor $e^{-i\varphi(k_x,k_y)}$ or $\exp(-1i\varphi(k_x,k_y))$ in Fourier domain.

At step 1650, a Fourier transform is applied to the updated target image propagated to the sample plane: $\sqrt{I_{ls}}e^{i\varphi_{ls}}$, and this data is updated in the corresponding region of higher-resolution solution $\sqrt{I_h}e^{i\varphi_h}$ in the Fourier space corresponding to the corresponding to the incidence wave vector $(k_x^i, k_y^i)$.

At step 1660, it is determined whether steps 1605 through 1650 have been completed for all aperture N locations. If steps 1605 through 1650 have not been completed for all aperture N locations, steps 1605 through 1650 are repeated for the next aperture location.

In most embodiments, the neighboring regions in Fourier space, which are iteratively updated for each aperture location, overlap each other. In the overlapping area between updated overlapping regions, the aperture scanning Fourier ptychographic system has multiple samplings over the same Fourier space. The aperture locations determine the area of the overlapping area. In one embodiment, the overlapping area between neighboring regions may have an area that is between 2% to 99.5% of the area of one of the neighboring regions. In another embodiment, the overlapping area between neighboring regions may have an area that is between 65% to 75% of the area of one of the neighboring regions. In another embodiment, the overlapping area between neighboring regions may have an area that is about 65% of the area of one of the neighboring regions. In certain embodiments, each overlapping region has the same area.

At step 1670, it is determined whether the solution for the higher-resolution image has converged. For example, convergence may be determined if the higher-resolution complex image is a self-consistent solution. In one case, the previous higher-resolution complex image of the previous iteration or initial guess is compared to the present higher-resolution solution, and if the difference is less than a certain value, the solution may have converged to a self-consistent solution. If it is determined that the solution has not converged, then steps 1605 through 1670 are repeated. In one embodiment, steps 1605 through 1670 are repeated once. In other embodiments, steps 1605 through 1670 are repeated twice or more. If the solution has converged, the converged solution in Fourier space is transformed to the spatial domain to recover a higher-resolution image $\sqrt{I_h}e^{i\varphi_h}$. If it is determined that the solution has converged at step 1570, then the method may proceed to optional step 1600, the method may end, or other optional additional step(s) may be performed such as additional defocus or aberration correction steps.

If the defocus distance is unknown, the aperture scanning Fourier ptychographic method can digitally adjust the 'z' parameter to different values based on a computation of the auto-focusing index from Eqn. 4. The aperture scanning Fourier ptychographic method can then construct the corresponding images, and select the sharpest image. This approach can also be extended to image a tiled sample. In this case, the aperture scanning Fourier ptychographic method can digitally adjust the 'z' parameter to achieve acuity for each tiled region of the whole image and combine the in-focus regions to form a fully focused image of the full field of view.

In other embodiments, alternative digital multiplicative phase factors can be included in multiplication steps 1605 and 1645 to correct for a variety of aberrations, as long as the factors correctly model the employed optics.

A limitation of conventional high-NA microscopes is a limited depth-of field. As an example, the depth-of-field of a conventional microscope with a 20× objective lens with 0.4 NA is about 5 μm. With a conventional microscope, resolution degrades as the sample moves away from the in-focus plane due to its limited depth-of-field. To achieve optimal resolution using a conventional microscope, the operator typically needs to move the stage to mechanically bring the sample back into focus. In this regard, a precise mechanical stage is needed in the conventional microscope to bring a sample into the in-focus position with sub-micron accuracy.

In certain embodiments, an aperture scanning Fourier ptychographic system implements an aperture scanning Fourier ptychographic method in which a sample can be refocused digitally rather than mechanically. In these cases, the aperture scanning Fourier ptychographic method computationally refocuses the out-of-focus sample during the recovery process. Using digital refocusing, the aperture scanning Fourier ptychographic system can expand its depth-of focus beyond the physical limitations of its optical element.

During operation of an aperture scanning Fourier ptychographic system, the z-position of the sample may not be known a priori. In certain aspects, an aperture scanning Fourier ptychographic method may include a digital autofocusing step that determines the z-position of the sample and uses this z-position to digitally refocus. For example, the aperture scanning Fourier ptychographic method of FIG. 8 may further comprise a step during or before step 1520 that computes the z-position of the sample. The aperture scanning Fourier ptychographic system may perform digital autofocusing by using a processor to perform steps 1520 and 1540 in FIG. 8 using the computed z-position of the sample. To compute the z-position of the sample, the aperture scanning Fourier ptychographic method determines an autofocusing index parameter. The auto-focusing index can be defined by the following equation:

$$\text{Auto-focusing index} = 1/\Sigma \text{abs}(\sqrt{I_{lf}} - \sqrt{I_{lfm}}) \quad \text{(Eqn. 2)}$$

Where: $\sqrt{I_{lf}}$ is the amplitude image from the low-pass filtering, and $\sqrt{I_{lfm}}$ is the actual intensity measurement The summation in Eqn. 2 is for all aperture locations. After the aperture scanning Fourier ptychographic method computes the estimated z-position of the sample, the aperture scanning Fourier ptychographic method can digitally refocus to the estimated z-position. In some cases, the recovered solution of the higher-resolution image has been found to converge more quickly when using an accurate z-position.

B) Another Example of a Recovery Process

FIG. 9B is a flowchart describes an example of alternate sub-steps of step 1500 of FIG. 8. In this case, step 1500 comprises step 1510, step 1530, step 1550, step 1560, step 1570, step 1580, and step 1590. Step 1500 may optionally comprise steps 1520 and 1540. Optional steps 1520 and 1540 may be performed if the sample is out-of-focus by the amount of $z_0$. One or more of the sub-steps in FIG. 9B can be performed by a processor.

At step 1510, low-pass filtering of the higher-resolution image $\sqrt{I_h}e^{i\varphi_h}$ in the Fourier domain is performed to generate a low-resolution image $\sqrt{I_l}e^{i\varphi_l}$ for a particular aperture location associated with a wave vector ($k_x^i$, $k_y^i$). The Fourier transform of the higher-resolution image is $\tilde{I}_h$ and the Fourier transform of the low-resolution image for a particular aperture location is $\tilde{I}_l$. In the Fourier domain, the aperture scanning Fourier ptychographic method filters a low-pass region from the spectrum $\tilde{I}_h$ of the higher-resolution image $\sqrt{I_h}e^{i\varphi_h}$. In cases with an optical element in the form of an objective lens, this region may be a circular aperture with a radius of NA*$k_0$, where $k_0$ equals $2\pi/\lambda$ (the wave number in vacuum), given by the coherent transfer function of an objective lens. In Fourier space, the location of the low-pass region corresponds to the aperture location. The region may be centered about a position ($-k_x^i$, $-k_y^i$) in the Fourier domain of $\sqrt{I_h}e^{i\varphi_h}$.

At optional step 1520, the low-resolution image, $\sqrt{I_l}e^{i\varphi_l}$ is propagated in the Fourier domain to the in-focus plane at z=0 of the optical element to determine the low-resolution image at the focused position: $\sqrt{I_{lf}}e^{i\varphi_{lf}}$. In one embodiment, Step 1520 can be performed by Fourier transforming the low-resolution image $\sqrt{I_l}e^{i\varphi_l}$, multiplying by a phase factor in the Fourier domain, and inverse Fourier transforming to obtain $\sqrt{I_{lf}}e^{i\varphi_{lf}}$. In another embodiment, step 1520 can be performed by the mathematically equivalent operation of convolving the low-resolution image $\sqrt{I_l}e^{i\varphi_l}$ with the point-spread-function for the defocus. In another embodiment, step 1520 can be performed as an optional sub-step of step 1510 by multiplying by multiplying $\tilde{I}_l$ by a phase factor in the Fourier domain before performing the inverse Fourier transform to produce $\sqrt{I_{lf}}e^{i\varphi_{lf}}$. Optional step 1520 need not be included if the sample is located at the in-focus plane (z=0) of the optical element.

At step 1530, the computed amplitude component $\sqrt{I_{lf}}$ of the low-resolution image at the in-focus plane, $\sqrt{I_{lf}}e^{i\varphi_{lf}}$, is replaced with the square root of the low-resolution intensity measurement $\sqrt{I_{lfm}}$ measured by the radiation detector of the aperture scanning Fourier ptychographic system. This forms an updated low resolution target: $\sqrt{I_{lfm}}e^{i\varphi_{lf}}$.

At optional step 1540, the updated low-resolution image $\sqrt{I_{lfm}}e^{i\varphi_{lf}}$ may be back-propagated to the sample plane (z=$z_0$) to determine $\sqrt{I_{ls}}e^{i\varphi_{ls}}$. Optional step 1540 need not be included if the sample is located at the in-focus plane of the optical element, that is, where $z_0$=0. In one case, step 1540 can be performed by taking the Fourier transform of the updated low-resolution image $\sqrt{I_{lfm}}e^{i\varphi_{lf}}$ and multiplying in the Fourier space by a phase factor, and then inverse Fourier transforming it. In another case, step 1540 can be performed by convolving the updated low-resolution image $\sqrt{I_{lfm}}e^{i\varphi_{lf}}$ with the point-spread-function of the defocus. In another case, step 1540 can be performed as a sub-step of step 1550 by multiplying by a phase factor after performing the Fourier transform onto the updated target image.

At step 1550, a Fourier transform is applied to the updated target image propagated to the sample plane: $\sqrt{I_{ls}}e^{i\varphi_{ls}}$, and this data is updated in the corresponding region of higher-resolution solution $\sqrt{I_h}e^{i\varphi_h}$ in the Fourier space corresponding to the corresponding to the incidence wave vector ($k_x^i$, $k_y^i$) and associate aperture location.

At step 1560, it is determined whether steps 1510 through 1560 have been completed for all N aperture locations. If steps 1510 through 1560 have not been completed for all N aperture locations, steps 1510 through 1560 are repeated for the next aperture location.

In most embodiments, the neighboring regions in Fourier space, which are iteratively updated for each aperture location, overlap each other. In the overlapping area between updated overlapping regions, the aperture scanning Fourier ptychographic method system has multiple samplings over the same Fourier space. The aperture locations determine the area of the overlapping area. In one embodiment, the overlapping area between neighboring regions may have an area that is between 2% to 99.5% of the area of one of the neighboring regions. In another embodiment, the overlapping area between neighboring regions may have an area that is between 65% to 75% of the area of one of the neighboring regions. In another embodiment, the overlapping area between neighboring regions may have an area that is about 65% of the area of one of the neighboring regions. In certain embodiments, each overlapping region has the same area.

At step 1570, it is determined whether the solution for the higher-resolution image has converged. For example, convergence may be determined if the higher-resolution complex image is a self-consistent solution. In one case, the previous higher-resolution complex image of the previous iteration or initial guess is compared to the present higher-resolution solution, and if the difference is less than a certain value, the solution may have converged to a self-consistent solution. If it is determined that the solution has not converged, then steps 1510 through 1570 are repeated. In one embodiment, steps 1510 through 1560 are repeated once. In other embodiments, steps 1510 through 1560 are repeated twice or more. If the solution has converged, the processor transforms the converged solution in Fourier space to the spatial domain to recover a higher-resolution image $\sqrt{I_h}e^{i\varphi_h}$. If the processor determines that the solution has converged at step 1570, then the process may proceed to optional step 1600, the method may end, or other optional additional step(s) may be performed such as additional defocus or aberration correction steps.

C) Tile Imaging

In some embodiments, an aperture scanning Fourier ptychographic method may include a tile imaging process that divides the captured intensity images into a plurality of intensity tile images, independently acquires a higher-resolution image for each of the tiles, and then combines the higher-resolution tile images to generate a full field-of-view higher-resolution image. In some cases, the higher-resolution tile images may be combined with an image blending process. An example of an image blending process is alpha blending which can be found in PCT publication WO1999053469, entitled "A system and method for performing blending using an over sampled buffer," filed on Apr. 7, 1999, which is hereby incorporated by reference in its entirety for this example. Since the higher-resolution images of the tiles may be acquired independently, this aperture scanning Fourier ptychographic method may allow for parallel computing, which may reduce computation time, and may also reduce memory requirements. Moreover, the light from each light element may be accurately treated as a plane wave for each tile. The incident wavevector for each tile can be expressed as:

$$(k_x^i, k_y^i) = \frac{2\pi}{\lambda}\left(\frac{(x_c - x_i)}{\sqrt{(x_c - x_i)^2 + (y_c - y_i)^2 + h^2}}, \frac{(y_c - y_i)}{\sqrt{(x_c - x_i)^2 + (y_c - y_i)^2 + h^2}}\right)$$ (Eqn. 1)

where $(x_c, y_c)$ is the central position of each tile of the full field-of-view intensity image, $(x_i, y_i)$ is the position of the $i^{th}$ light element, and h is the distance between the illuminator and the sample. Furthermore, this aperture scanning Fourier ptychographic method can assign a specific aberration-correcting pupil function to each tile in some cases.

Figure 10:
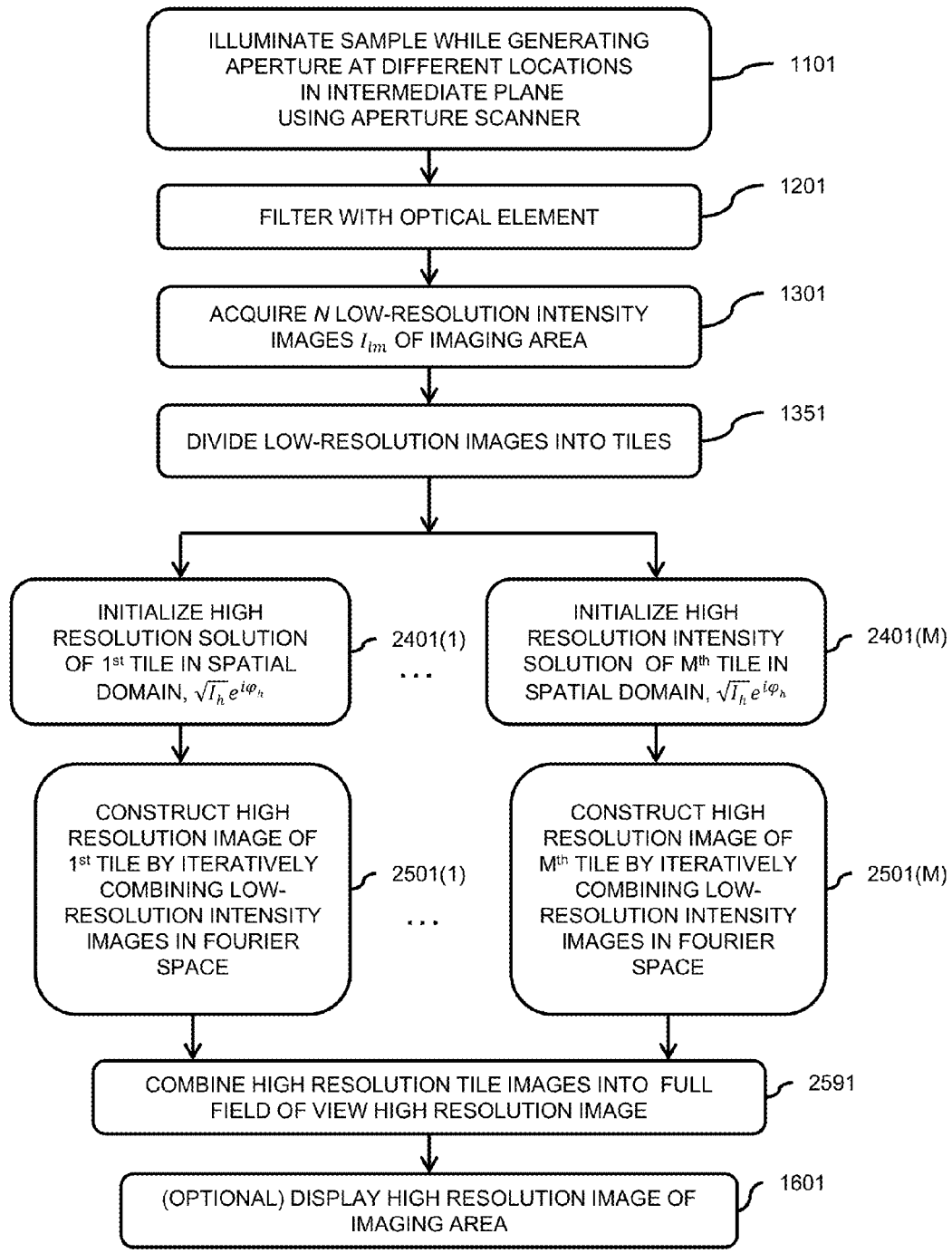
FIG. 10 is a flowchart of an aperture scanning Fourier ptychographic method with tile imaging, according to certain aspects.

FIG. 10 is a flowchart of an aperture scanning Fourier ptychographic method with tile imaging, according to certain aspects. This aperture scanning Fourier ptychographic method can be performed by an aperture scanning Fourier ptychographic system. To take advantage of parallel processing capabilities, the aperture scanning Fourier ptychographic system used to perform the method comprises a processor with parallel processing capabilities such as, for example, the GPU unit or a processor having multiple cores (i.e. independent central processing units). In this example, the aperture scanning Fourier ptychographic method comprises a measurement process (steps 1101, 1201, and 1301), a recovery process (steps 1351, 2401 (i-M), 2501(i-M), 2591), and an optional display process (step 1601). The measurements process (steps 1101, 1201, and 1301) and display process (step 1600) are similar to those steps described with reference to FIG. 8.

At step 1351, the processor divides the full field-of-view into a plurality of tiles such as, for example, a two-dimensional matrix of tiles. The dimensions of a two-dimensional square matrix of tiles may be in powers of two such as, for example, a 256 by 256 matrix, a 64×64 matrix, etc. In one example, the processor may divide up a full field of view of 5,280×4,380 pixels into tiles having an area of 150×150 pixels.

Next, the processor initializes the higher-resolution image: $\sqrt{I_h}e^{i\varphi_h}$ in the spatial domain for each tile (1 to M) independently using parallel computing (step 2400(1) . . . step 2400(M)). A Fourier transform is applied to the initial guess. In some cases, the initial guess may be determined as a random complex matrix (for both intensity and phase). In other cases, the initial guess may be determined as an interpolation of the intensity measurement with a random phase. An example of an initial guess is $\varphi=0$ and $I_{h,r}$ of any intensity image of the sample area. Another example of an initial guess is a constant value. The Fourier transform of the initial guess can be a broad spectrum in the Fourier domain.

At step 2501(1) . . . step 2501(M), the processor computationally constructs a higher-resolution image of each tile (1 to M) independently using parallel computing. The processor computationally constructs the higher-resolution image of each tile by iteratively combining intensity images in Fourier space. Steps 1521 and 1541 may be included if sample out of focus.

At step 2591, the processor combines the higher-resolution tile images into a full field-of view higher-resolution image. In some cases, combining tile images comprises an imaging-blending process such as, for example, alpha blending.

Color imaging capability is pivotal in pathology and histology. In certain embodiments, an aperture scanning Fourier ptychographic system 10 capable of color imaging comprises an illumination source that can provide red, green, and blue illuminations. The aperture scanning Fourier ptychographic method combines the higher-resolution image results from red, green, and blue LED illumination into each corresponding color channel to form a final higher-resolution color image. Three images are generated corresponding to red, green, and blue, which are combined to form a higher resolution color image.

VI. Subsystems

Figure 11:
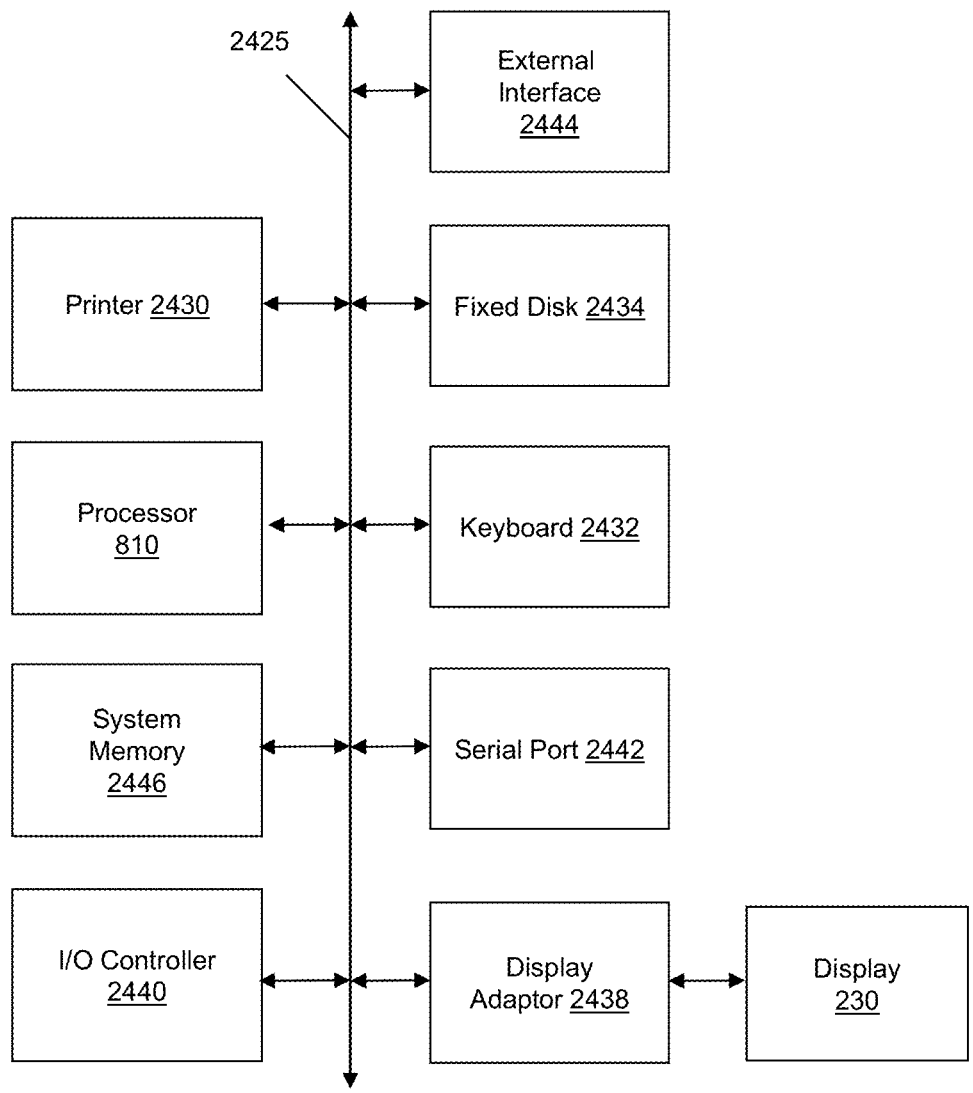
FIG. 11 is a block diagram of subsystems that may be present in aperture-scanning Fourier ptychography imaging system.

FIG. 11 is a block diagram of subsystems that may be present in certain aperture scanning Fourier ptychographic systems described herein. For example, an aperture scanning Fourier ptychographic system may include a processor. The processor may be a component of the aperture scanning Fourier ptychographic system in some cases. The processor may be a component of the radiation detector in some cases.

The various components previously described in the Figures may operate using one or more of the subsystems to facilitate the functions described herein. Any of the components in the Figures may use any suitable number of subsystems to facilitate the functions described herein. Examples of such subsystems and/or components are shown in a FIG. 11. The subsystems shown in FIG. 11 are interconnected via a system bus 2425. Additional subsystems such as a printer 2430, keyboard 2432, fixed disk 2434 (or other memory comprising computer readable media), display 830, which is coupled to display adapter 2438, and others are shown. Peripherals and input/output (I/O) devices, which couple to I/O controller 2440, can be connected by any number of means known in the art, such as serial port 2442. For example, serial port 2442 or external interface 2444 can be used to connect the computing device 200 to a wide area network such as the Internet, a mouse input device, or a scanner. The interconnection via system bus 2425 allows the processor to communicate with each subsystem and to control the execution of instructions from system memory 2446 or the fixed disk 2434, as well as the exchange of information between subsystems. The system memory 2446 and/or the fixed disk 2434 may embody the CRM 220 in some cases. Any of these elements may be present in the previously described features.

In some embodiments, an output device such as the printer 2430 or display 830 of the aperture scanning Fourier ptychographic system can output various forms of data. For example, the aperture scanning Fourier ptychographic system can D color/monochromatic images (intensity and/or phase), data associated with these images, or other data associated with analyses performed by the aperture scanning Fourier ptychographic system.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM, such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A Fourier ptychographic imaging device, comprising:
   a first lens configured to receive light issuing from a sample being imaged while the sample is illuminated by an illumination source during operation;
   a spatial light modulator configured to generate, during operation, an aperture in an intermediate plane at a plurality of aperture locations at different acquisition times, the aperture configured to transmit light transmitted by the first lens during operation, wherein the plurality of aperture locations correspond to overlapping regions in the Fourier domain;
   a second lens configured to receive, during operation, light transmitted by the aperture; and
   a radiation detector configured to receive light transmitted by the second lens and to acquire a plurality of intensity measurements during operation.

2. The Fourier ptychographic imaging device of claim 1, further comprising a processor configured to execute, during operation, instructions for constructing a complex image of the sample being imaged using the acquired intensity measurements.

3. The Fourier ptychographic imaging device of claim 2, wherein the complex image is constructed by iteratively updating the overlapping regions in Fourier domain with data from the acquired intensity measurements during operation.

4. The Fourier ptychographic imaging device of claim 1, wherein the spatial light modulator comprises a reflective liquid-crystal on silicon display or a digital micromirror device for providing the aperture.

5. The Fourier ptychographic imaging device of claim 1, wherein the intermediate plane is a Fourier plane to a sample plane of the sample being imaged.

6. The Fourier ptychographic imaging device of claim 1, wherein each of the plurality of intensity measurements acquired by the radiation detector uniquely corresponds to a different aperture location of the plurality of aperture locations.

7. The Fourier ptychographic imaging device of claim 1, wherein:
   the first lens is a convex lens having a first focal length and is located with an optical the first focal length from the sample plane,
   the second lens is a convex lens having a second focal length and is located the second focal length from the intermediate plane,
   the intermediate plane is located the first focal length away from the first lens, and
   the intermediate plane is located the second focal length away from the second lens.

8. The Fourier ptychographic imaging device of claim 7, wherein the first focal length is approximately the same as the second focal length to form a 4f configuration.

9. The Fourier ptychographic imaging device of claim 7, wherein the radiation detector is located the first focal length from the second lens.

10. The Fourier ptychographic imaging device of claim 1, wherein the spatial light modulator is further configured to provide additional apertures, during operation, to form a plurality of apertures at at least one acquisition time,
   wherein the second lens receives light, during operation, transmitted through the plurality of apertures at the at least one of the acquisition times, wherein the acquired intensity measurement at the at least one acquisition time is associated with light transmitted through the corresponding plurality of apertures.

11. The Fourier ptychographic imaging device of claim 1, wherein the overlapping areas in the Fourier domain overlap by at least about 70% of the aperture area.

12. The Fourier ptychographic imaging device of claim 1, wherein overlapping areas in the Fourier domain overlap by between 20% and 90% of the aperture area.

13. The Fourier ptychographic imaging device of claim 1, wherein the illumination source and the first lens are on one side of the sample being imaged.

14. The Fourier ptychographic imaging device of claim 1, wherein the spatial light modulator comprises a display located at the intermediate plane, the display configured to display the aperture during operation.

15. The Fourier ptychographic imaging device of claim 1, wherein the spatial light modulator is a digital micromirror device having one or more mirrors, wherein the digital micromirror device is configured to rotate one or more of the mirrors during operation to position the mirrors such that light is transmitted through the aperture in the intermediate plane and reflected from one or more of the mirrors at other locations in the intermediate plane.

16. A Fourier ptychographic imaging method, comprising:

causing an aperture to be located at a plurality of locations at a plurality of acquisition times, wherein the aperture is located at about a Fourier plane to a sample plane of a sample being imaged, wherein the aperture receives light issuing from the illuminated sample through a first lens during operation, wherein the plurality of locations correspond to overlapping regions in the Fourier domain; and constructing an image of the sample by iteratively updating the overlapping regions in the Fourier domain with a plurality of intensity measurements taken by a radiation detector at the plurality of acquisition times, the plurality of intensity measurements based on light focused by a lens that is transmitted through the aperture at the plurality of acquisition times.

17. The Fourier ptychographic imaging method of claim 16, further comprising generating additional apertures at the Fourier plane to form a plurality of apertures at each acquisition time.

18. The Fourier ptychographic imaging method of claim 16, wherein the plurality of intensity measurements captured by the radiation detector uniquely correspond to different aperture locations of the plurality of aperture locations.

19. The Fourier ptychographic imaging method of claim 16, wherein the overlapping areas in the Fourier domain overlap by at least about 70% of an area of the aperture.

20. The Fourier ptychographic imaging methon of claim 16, wherein constructing the image of the sample comprises:
(a) initializing a current image in the Fourier domain;
(b) filtering an overlapping region of the current image in the Fourier domain to generate an intensity image for a corresponding aperture location of the plurality of aperture locations;
(c) replacing the data of the intensity image with an intensity measurement; and
(d) updating the overlapping region in the Fourier domain with the intensity image based on the intensity measurement.

21. The Fourier ptychographic imaging method of claim 16, wherein causing the aperture to be located at a plurality of locations at the plurality of acquisition times comprises activating display elements of a reflective liquid-crystal on silicon display corresponding to the respective location.

22. The Fourier ptychographic imaging method of claim 16, wherein causing the aperture to be located at a plurality of locations at the plurality of acquisition times comprises rotating one or more micromirrors of a digital micromirror device to an angular position corresponding to the respective location.

* * * * *

UNITED STATES PATENT AND TRADEMARK OFFICE
CERTIFICATE OF CORRECTION

PATENT NO.           : 9,983,397 B2                                    Page 1 of 1
APPLICATION NO.      : 15/206859
DATED                : May 29, 2018
INVENTOR(S)          : Roarke Horstmeyer et al.

It is certified that error appears in the above-identified patent and that said Letters Patent is hereby corrected as shown below:

In the Claims

In Claim 20, Column 36, Line 1, please replace the word "methon" with the word --method--

Signed and Sealed this
Second Day of July, 2019

Andrei Iancu
*Director of the United States Patent and Trademark Office*